United States Patent
Von Andrian et al.

(10) Patent No.: US 9,872,905 B2
(45) Date of Patent: Jan. 23, 2018

(54) MODULATION OF NK CELL ANTIGEN SPECIFIC EFFECTOR ACTIVITY BY MODULATION OF CXCR6 (CD186)

(75) Inventors: Ulrich Von Andrian, Chestnut Hill, MA (US); Silke Paust, Jamaica Plain, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 343 days.

(21) Appl. No.: 13/512,754

(22) PCT Filed: Dec. 1, 2010

(86) PCT No.: PCT/US2010/058561
§ 371 (c)(1),
(2), (4) Date: Jan. 9, 2013

(87) PCT Pub. No.: WO2011/068870
PCT Pub. Date: Jun. 9, 2011

(65) Prior Publication Data
US 2013/0101597 A1    Apr. 25, 2013

Related U.S. Application Data

(60) Provisional application No. 61/265,669, filed on Dec. 1, 2009.

(51) Int. Cl.
| | |
|---|---|
| A61K 39/00 | (2006.01) |
| A61K 39/395 | (2006.01) |
| A61K 45/06 | (2006.01) |
| C07K 16/28 | (2006.01) |
| A61K 38/19 | (2006.01) |
| C12Q 1/02 | (2006.01) |
| A61K 38/17 | (2006.01) |

(52) U.S. Cl.
CPC ............ *A61K 45/06* (2013.01); *A61K 38/177* (2013.01); *A61K 38/195* (2013.01); *A61K 39/3955* (2013.01); *C07K 16/2866* (2013.01); *C12Q 1/025* (2013.01); *A61K 2039/505* (2013.01)

(58) Field of Classification Search
None
See application file for complete search history.

(56) References Cited

U.S. PATENT DOCUMENTS

2003/0165995 A1* 9/2003 Briskin et al. .................. 435/7.1
2005/0289661 A1* 12/2005 Allen .............................. 800/18

FOREIGN PATENT DOCUMENTS

WO    01/37872 A1    5/2001
WO    08/146272 A2   12/2008

OTHER PUBLICATIONS

Petit et al. 'Site-directed mutagenesis of the chemokine receptor CXCR6 suggests a novel paradigm for interactions with the ligand CXCL16.' Eur. J. Immunol. 38:2337-2350, 2008.*
Cooper, Megan A. et al., "Cytokine-induced memory-like natural killer cells," PNAS, vol. 106(6):1915-1919 (2009).
Kurtz, Joachim, "Specific memory within innate immune systems," Trends in Immunology, vol. 26(4):186-192 (2005).
O'Leary, Jacqueline G. et al., "T cell- and B cell-independent adaptive immunity mediated by killer cells," Nature Immunology, vol. 7(5):507-516 (2006).
Paust, Silke et al., "Adaptive immune responses mediated by natural killer cells," Immunological Reviews, vol. 235:286-296 (2010).
Paust, Silke et al., "Critical role for the chemokine receptor CXCR6 in NK cell-mediated antigen-specific memory of haptens and viruses," Nature Immunology, vol. 11(12):1127-1136 (2010).
Raulet, David H., "Natural Killer Cells: Remembrances of Things Past," Current Biology, vol. 19(7):R294-R296 (2009).
Sun, Joseph C. et al., "Adaptive immune features of natural killer cells," Nature, vol. 457:557-561 (2009).
Sun, Joseph C. et al., "Immune memory redefined: characterizing the longevity of natural killer cells," Immunological Reviews, vol. 236:83-94 (2010).
Sun, Joseph C. et al., "Natural killer cells remember: An evolutionary bridge between innate and adaptive immunity?" Eur. J. Immunol., vol. 39:2059-2064 (2009).
International Search Report and Written Opinion for Application No. PCT/US2010/058561, 16 pages, dated Jul. 8, 2011.
International Preliminary Report on Patentability and Written Opinion for Application No. PCT/US2010/058561, 10 pages, dated Jun. 5, 2012.
Fagan et al., "Immunotherapy for cancer: the use of lymphokine activated killer (LAK) cells" , Gut. 1987, 28:113-116.
Mombaerts et al., "RAG-1-Deficient Mice Have no Mature B and T Lymphocytes" Cell, 1992, 68(5):869-877.

* cited by examiner

*Primary Examiner* — Nora Rooney
(74) *Attorney, Agent, or Firm* — McCarter & English, LLP; Maria Laccotripe Zacharakis; Briana M. Erickson

(57) ABSTRACT

The instant invention is based, at least in part, on the discovery that CXCR6 plays a critical role in antigen-specific effector function of NK cells. Accordingly, the invention provides, among other things, methods for modulation of antigen-specific NK cell effector function, methods for identifying modulators of antigen-specific NK cell effector function.

17 Claims, 28 Drawing Sheets

MODULATION OF NK CELL ANTIGEN SPECIFIC EFFECTOR ACTIVITY BY MODULATION OF CXCR6 (CD186)

RELATED APPLICATIONS

This application claims the benefit of priority to U.S. Ser. No. 61/265,669, filed on Dec. 1, 2009. The contents of this application are incorporated by reference herein.

GOVERNMENT FUNDING

Work described herein was supported, at least in part, under grant AIO69259 awarded by the National Institutes of Health. The U.S. government, therefore, has certain rights in this invention.

BACKGROUND OF THE INVENTION

Immune responses to infectious or damaging agents are commonly categorized as being mediated either by the innate arm of the immune system or the adaptive arm of the immune system. The innate immune system is distinguished from the adaptive immune system in that it uses a finite number of germ line encoded receptors to sense pathogens and tissue damage. Innate immune responses are not selected for high affinity interactions between immune cells or pathogens and do not lead to immunological memory. In contrast, the adaptive immune system relies on non-homologous end-joining and chromosomal DNA recombination in a recombinase activating gene (RAG)-dependent manner to generate T and B cell receptor repertoire that recognize a vast number of different antigens. Activation of T and B cells by their specific antigen leads to the selection of high affinity effector and memory cells, resulting in accelerated and enhanced, antigen specific recall responses upon challenge, another hallmark of the adaptive immune system.

Adaptive immune responses occur to a variety of antigens, including infectious pathogens and non-infectious substances, and even organic or inorganic molecules, such as 2,4-dinitro-1-fluorobenzene (DNFB) and 4-ethoxy-methylene-2-phenyl-3-oxazalin-5-one (OXA). These so called haptens form covalent bonds with amino acid side-chains of self-proteins, and are recognized as altered-self by the immune system. DNFB and OXA are classic examples of contact sensitizers that elicit delayed type hypersensitivity (DTH) responses, specifically hapten-induced contact hypersensitivity (CHS). Typically, the first exposure to hapten results in sensitization, while a second exposure to the same hapten triggers an adaptive immune response, associated with tissue swelling at the site of challenge caused by the recruitment of inflammatory cells.

Until recently, there has been no evidence that any types of cells other than T and B cells could give rise to adaptive immune responses, characterized by antigen specificity and memory, in mammals. However, it has now been demonstrated that mice devoid of T cells and B cells can demonstrate substantial contact hypersensitivity (CHS) responses to haptens (O'Leary et al. 2006. Nature Immunology 7:507). These CHS responses were found to be both adaptive and antigen specific. Mice lacking all lymphocytes, including natural killer cells, did not display CHS responses. Adoptive transfer experiments demonstrated that the hapten-specific memory in the mice lacking T and B cells resided in a Ly49C-I+ natural killer subpopulation localized specifically in the livers of the animals.

Further information regarding the capacity of NK cells to mediate adaptive immune responses, the types of antigens to which they can mount antigen-specific responses, and the signals required to mediate such responses will be of tremendous benefit in controlling antigen-specific NK cell responses. Knowing this information will allow, inter alia, for augmentation of antigen-specific NK cell effector function in subjects that would benefit from increased NK cell activity, e.g., in immunodeficient subjects, as well as reducing antigen-specific NK cell effector function in subjects that suffer from unwanted immune system activation, e.g., in the case of CHS responses.

SUMMARY OF THE INVENTION

The instant invention is based, at least in part, on the discovery that NK cells mediate antigen specific memory responses to a variety of antigens, and that NK cell mediated adaptive immune responses are critically dependent on CXCR6.

In one aspect, the invention pertains to A method of modulating antigen-specific NK cell function in a subject comprising administering a composition comprising an agent that upmodulates or downmodulates antigen-specific NK cell function to the subject such that antigen-specific NK cell function is modulated, wherein the subject is tested to determine the level or function of antigen specific NK cells prior to or after administration of the composition.

In one embodiment, antigen-specific NK cell function is reduced. In one embodiment, antigen-specific NK cell function is increased.

In another aspect, the invention pertains to a method of decreasing antigen-specific NK cell function in a subject having unwanted immune cell activation, comprising administering to the subject a composition comprising an agent that downmodulates antigen-specific NK cell function to the subject such that antigen-specific NK cell function is decreased.

In one embodiment, the subject has delayed-type hypersensitivity to an antigen or is at risk for developing delayed-type hypersensitivity to an antigen.

In one embodiment, the antigen is a hapten.

In one embodiment, the step of administering is performed after secondary exposure to the antigen and prior to the onset of a delayed-type hypersensitivity reaction.

In one embodiment, the step of administering is performed after secondary exposure to the antigen and after onset of a delayed-type hypersensitivity reaction.

In one embodiment, the step of administering is performed prior to secondary exposure to the antigen.

In one embodiment, the subject suffers from an occupational allergy.

In one embodiment, the step of administering is performed more than once.

In one embodiment, the method further comprises administration of an immunosuppressive agent that inhibits activation of one or more of: T cells, B cells, dendritic cells, and NK cells.

In one embodiment, subject does not respond adequately to said immunosuppressive agent when administered alone.

In one embodiment, the subject has or is at risk for developing a deleterious immune response to an infectious agent. In one embodiment, infectious agent is a virus. In one embodiment, the infectious agent is a bacteria.

In one embodiment, the infectious agent is a virus selected from the group consisting of: hepatitis B virus, influenza virus, hepatitis C virus, varicella zoster, herpes virus, HIV1 and HIV2.

In one embodiment, the agent is selected from the group consisting of: an antibody that binds to an extracellular domain of human CXCR6 and blocks the binding of CXCR6 to the extracellular domain of CXCL16; an antibody that binds to the extracellular domain of CXCL16 and blocks the binding of CXCL16 with an extracellular domain of CXCR6; a nucleic acid molecule which mediates RNA interference of the CXCR6 gene, a nucleic acid molecule which mediates RNA interference of the CXCL16 gene a nucleic acid molecule which is antisense to the CXCR6 gene, a nucleic acid molecule which is antisense to the CXCL16 gene, and a soluble CXCR6 molecule.

In another aspect, the invention pertains to a method of increasing antigen-specific NK cell function in a subject having low immune cell function, comprising administering to the subject a composition comprising an agent that upmodulates antigen-specific NK cell function to the subject such that antigen-specific NK cell function is increased.

In one embodiment, the subject is immunocompromised.

In one embodiment, the subject is deficient in T cell function. In one embodiment, the subject is deficient in B cell function. In another embodiment, the subject is deficient in T and B cell function.

In one embodiment, the composition comprises an antigen.

In one embodiment, the antigen is present on the surface of a cell.

In one embodiment, the antigen is processed antigen present on the surface of an antigen presenting cell.

In one embodiment, the composition further comprises an adjuvant.

In one embodiment, the antigen is derived from an infectious agent.

In one embodiment, the antigen is a tumor cell antigen.

In one embodiment, the antigen is viral antigen. In one embodiment, the antigen is a bacterial antigen. In one embodiment, the antigen is a parasite-derived antigen.

In one embodiment, the agent is a soluble form of CXCL16 which binds to and transduces a signal via CXCR6.

In another aspect, the invention pertains to a targeting composition comprising an agent that binds to CXCR6 and a ligand for an activating or inhibitory NK cell receptor.

In another embodiment, the invention pertains to a targeting composition comprising an agent that binds to CXCR6 and a modulator of NK cell function.

In another aspect, the invention pertains to a method for identifying agents that reduce antigen specific NK cell effector function comprising, i) contacting a cell expressing a functional CXCR6 molecule with an agent that binds to and transduces a signal via CXCR6 in the presence and absence of a test compound, ii) measuring signal transduction via CXCR6, iii) comparing the level of signal transduction via CXCR6 in the presence of the compound and the absence of the compound, iv) selecting those compounds that reduce signal transduction via CXCR6, v) testing the selected compounds for their ability to reduce antigen specific NK cell effector function, wherein a reduction in the level of antigen specific NK cell effector function in the presence of the test compound indicates that the compound reduces antigen specific NK cell effector function.

Immunization of C57BL/6 Rag-KO mice with UV VSV significantly prolongs survival upon life challenge. Rag-KO mice were immunized day 0 with 5 ug UV VSV, and infected intravenously with 500 pfu life VSV 4 weeks post immunization. Twenty-four hours before challenge, mice were injected with 100 ug anti-CXCR6 or isotype control mAb, and infected intranasally with 2,500 pfu (Rag-KO B6 and DKO B6/B10), or 10,000 pfu (Rag-KO Balb/c) Influenza A virus, and their survival determined.

Figure 5A:
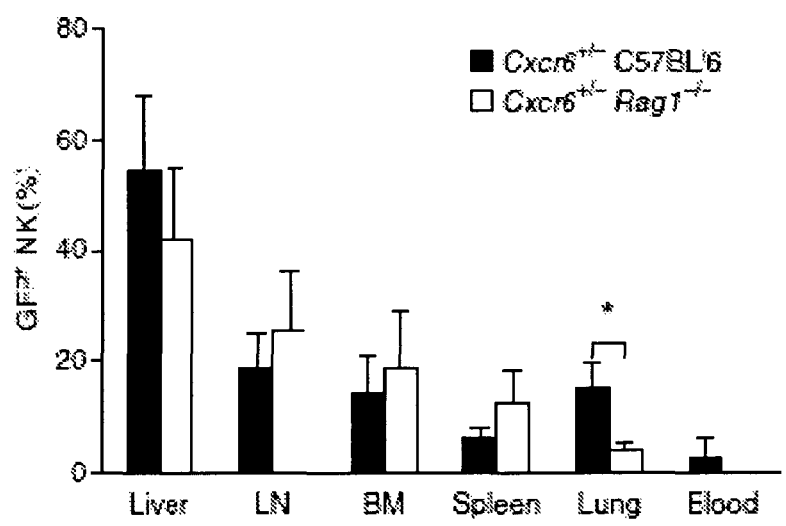
Figure 5B:
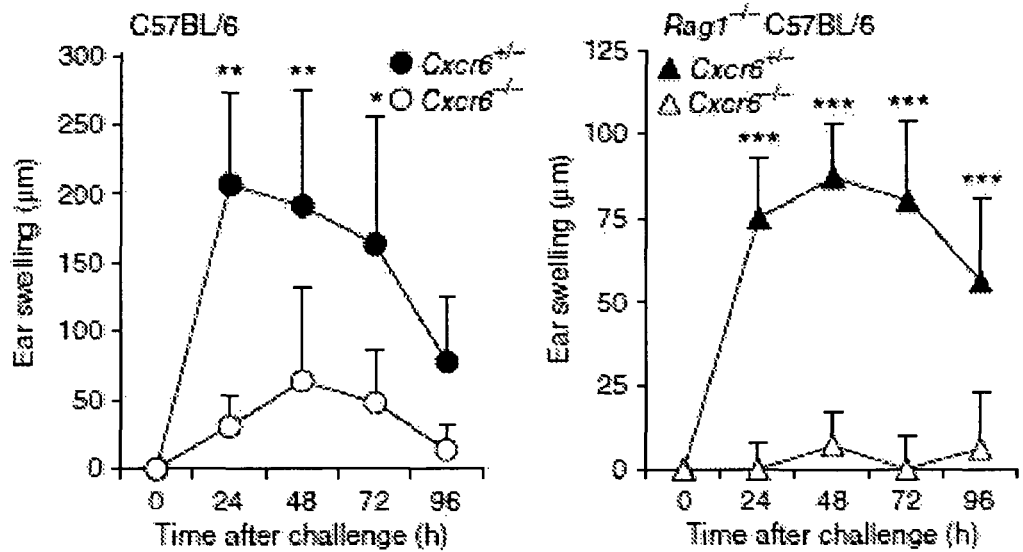
Figure 5C:
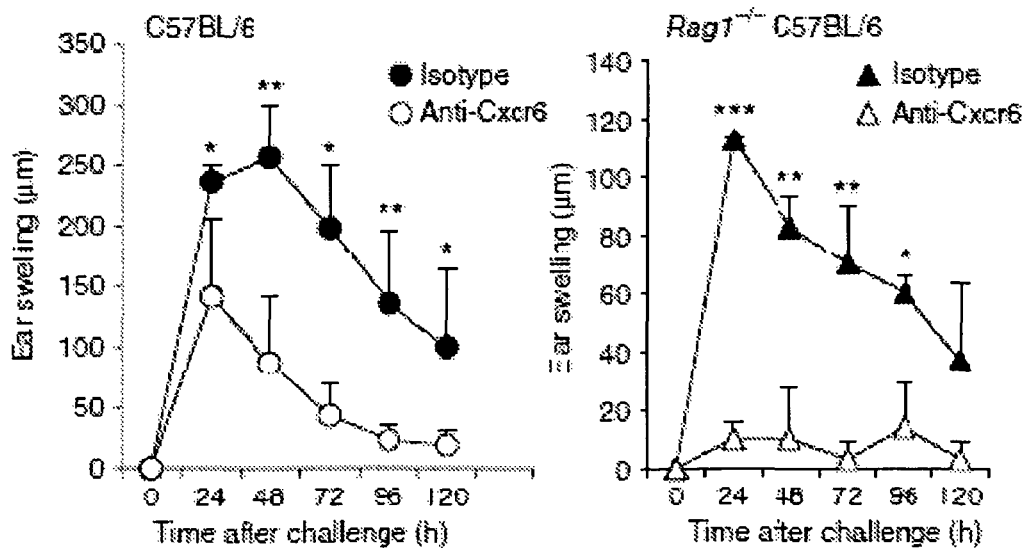

FIG. 5. NK cell-expressed CXCR6 is required for NK cell-mediated adaptive immunity to haptens. Panel (a) shows that the frequency of CXCR6-expressing CD45+ NK1.1+ NK cells from Cxcr6+/– mice on a Rag1-sufficient (C57BL/6) or Rag1–/– background in different tissues, assessed by flow cytometry. LN, lymph node; BM, bone marrow. (b) DNFB-induced CHS in lymphocompetent C57BL/6 mice (left) and Rag1–/– C57BL/6 mice (right; n=10-12 mice per group). (c) DNFB-induced CHS in C57BL/6 mice (left) and Rag1–/– C57BL/6 mice (right) sensitized with hapten and given mAb to CXCR6 (100 ig per mouse) or isotype-matched control antibody intravenously 24 h before DNFB challenge (n=10-15 mice per group). *P<0.01, P<0.001 and *P<0.0001 (unpaired Student's t-test (a,c,d) or ANOVA (b)). Data are representative of three to five independent experiments (pooled results; error bars, s.d.).

Figure 6A:
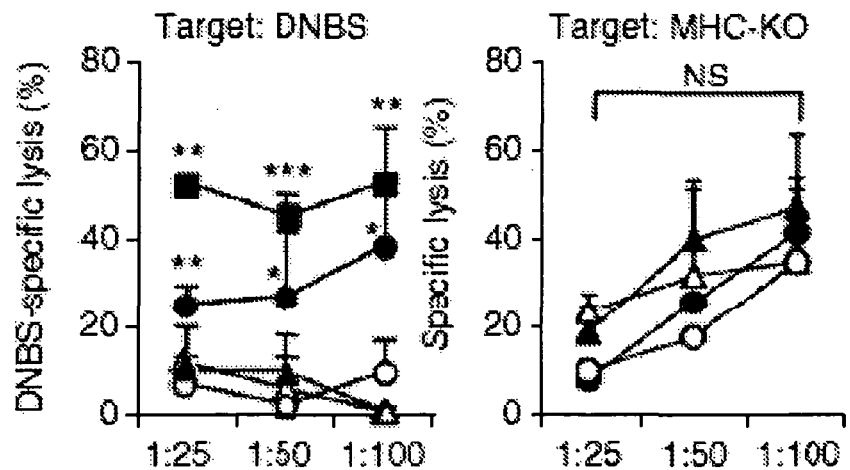

FIG. 6. Hepatic memory NK cells mediate hapten-specific killing in vitro. Panel (a) shows killing capacity of DNFB-primed hepatic CD45+ NK1.1+ NK cells from Cxcr6+/– or Cxcr6–/– donor mice (n=12 donor mice per group), assessed as in a in the presence of mAb to CXCR6 or isotype-matched control mAb. *P<0.01, P<0.001 and *P<0.00001, compared with Cxcr6–/– (unpaired Student's t-test). (b) Killing capacity of acetone- or DNFB-primed hepatic CD45+ NK1.1+ NK cells from Rag1–/– donors (n=15 per group) at a target cell/effector cell ratio of 1:25, assessed in the presence of mAb to CXCR6 (10 μg/ml), mAb to CXCL16 (10 μg/ml) or CXCL16 (500 ng/ml); results are presented relative to those of cultures treated with isotype-matched control antibody (10 μg/ml). *P<0.01 and **P<0.001, compared with isotype-matched control antibody (unpaired Students t-test).

Figure 7A:
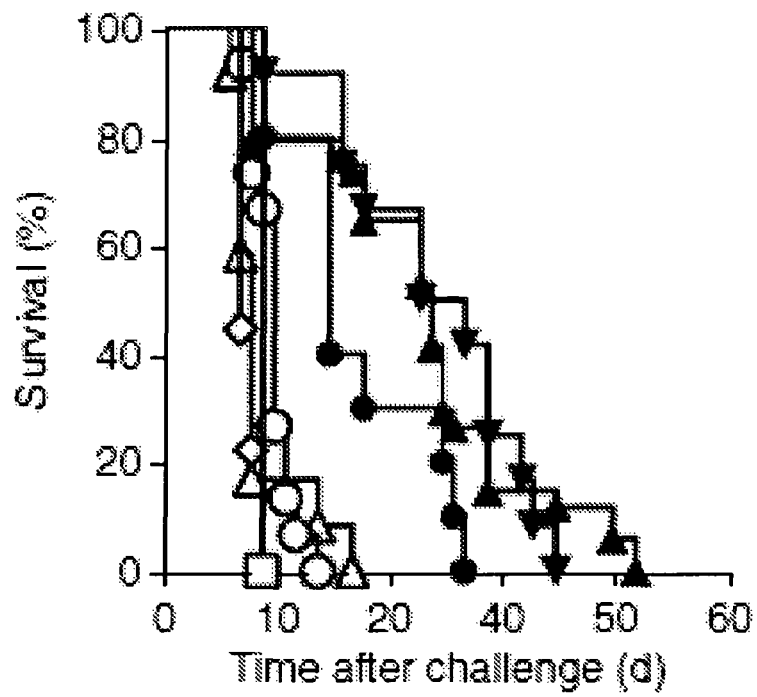
Figure 7B:
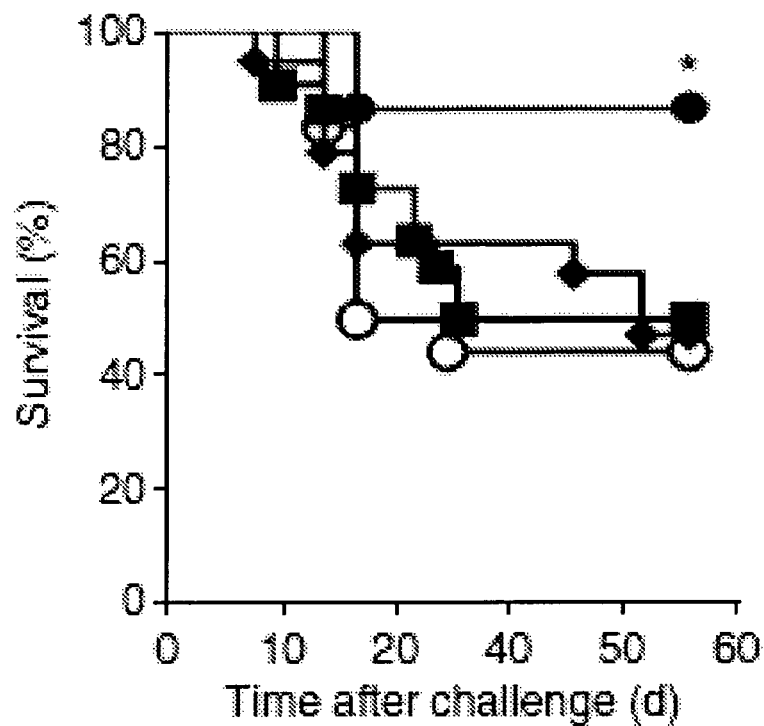

FIG. 7. Liver NK cells develop specific memory of viral antigens. Panel (a) shows survival of Rag1–/– mice (n=8-12 per group) immunized with PR8-VLPs, M1-VLPs or UV-VSV, then challenged 1 month later with live virus (2,500 PFU influenza strain A/PR/8/34 intranasally or 500 PFU VSV intravenously). P values, log-rank Mantel-Cox test. (b) Survival of Rag2–/– mice (n=15-22 per group) immunized with VLPs containing influenza (PR8-VLP) or HIV-1 (HIV-VLP) or with UV-VSV, then challenged 1 month later by intramuscular injection of VSV at the median lethal dose (250 PFU). *P=0.0116 (log-rank Mantel-Cox test).

FIG. 8. Mouse liver NK cells recognize and discriminate between HIV-1 and influenza A. Panel (a) shows that ear swelling in naive Rag2–/–Il2rg–/– mice (n=12-15 per group) that received adoptively transferred hepatic (left) or splenic (right) CD45+ NK1.1+ NK cells (8×104 cells per mouse) from Rag1–/– donor mice immunized with VLPs containing influenza (PR8) or HIV-1 (HIV) 1 month before transfer; recipients were challenged by subcutaneous injection of VLPs into one ear and PBS in the other ear and were assessed 2 months after transfer. NS, not significant; *P<0.01 and **P<0.001 (unpaired Student's t-test). (b) Ear swelling in C57BL/6 Rag1–/– mice (left) and BALB/c Rag2–/– mice (right) immunized with VLPs and challenged 1 month later (n=10-15 mice per group). P values, unpaired Student's t-test. Background ear swelling in nonimmunized mice was subtracted from ear swelling in the experimental groups. Data are representative of three to five independent experiments (pooled results; error bars, s.d.).

FIG. 9. Cell-expressed CXCR6 is required for NK cell-mediated adaptive immunity to viruses. Panel (a) shows that antiviral DTH responses in Rag1–/– C57BL/6 mice (left) or Rag2–/– BALB/c mice (right) immunized and challenged with various combinations of VLPs and UV-VSV (below graphs) and given mAb to CXCR6 (100 ig per mouse) or isotype-matched control antibody 24 h before challenge. P values, unpaired Student's t-test. (b) Survival of Rag1–/– and Rag2–/– mice (n=8-12 per group) immunized with PR8-VLP or M1-VLP, challenged 1 month later by lethal infection with influenza A strain A/PR/8/34 (2,500 PFU for Rag1–/– (left) and 10,000 PFU for Rag2–/– (right)) and injected with mAb to CXCR6 (100 ig per mouse) or isotype-matched control antibody on days 1 and 5. P values, log-rank Mantel-Cox test. Data are representative of three to five independent experiments (pooled results; error bars, s.d.).

Figure 10:
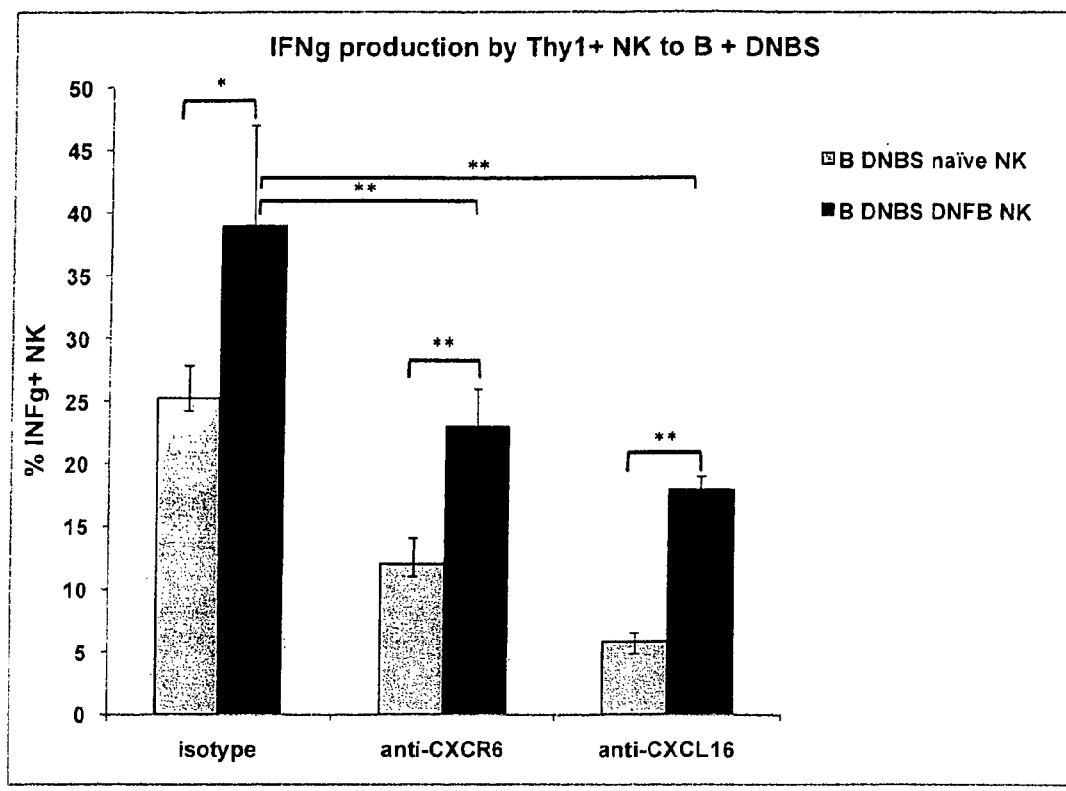

FIG. 10. IFN produced by the NK cells, whether naïve or stimulated, was reduced in the presence of an agent which blocks CXCR6, i.e., anti-CXCR6 or anti-CXCL16.

DETAILED DESCRIPTION OF THE INVENTION

As set forth above, the instant invention is based, at least in part, on the discovery that the CXCR6 pathway plays a critical role in antigen-specific effector activity by NK cells. More specifically, as described herein, CXCR6+ NK cells mediate antigen specific memory responses in vivo (both to haptens and complex antigens on infections agents (e.g., viruses)). The survival of adoptively transferred NK cells does not require prior sensitization and NK antigen specific memory responses do not depend on lymphopenia in the host. Long term survival of adoptively transferred NK cells occurs in the liver. NK cell expressed CXCR6 is required for antigen-specific responses; NK cell mediated killing is antigen specific and sensitization dependent, and restricted to hepatic NK cells. Blocking the interaction of CXCR6 and CXCL16 in vivo abrogates NK cell killing. Sensitized hepatic NK cells significantly prolong the survival of Rag/ $\gamma_c$-DKO recipients (lacking T and B cells) upon challenge with virus. NK cells distinguish among protein antigens in several backgrounds of Rag-KO mice. NK cell mediated influenza recognition does require CXCR6 and prolonged survival upon immunization occurs in several backgrounds of Rag-KO mice and is independent of HA, but dependent on CXCR6.

This discovery makes available, e.g., methods for modulating antigen-specific effector function of NK cells in patients that would benefit from modulation of antigen-specific NK cell function as well as novel methods for detecting new agents that can be used for this purpose.

I. Definitions

So that the invention may be more readily understood, certain terms are first defined.

As used herein, the term "modulating" with respect to antigen-specific NK cell mediated effector function includes upmodulating and downmodulating the effector function of NK cells. Modulated antigen specific NK cells have higher or lower effector function than prior to the modulation. For example, effector function can be altered using the claimed methods to be greater or less than what occurs absent intervention. Thus, the various forms of the term "modulate" include stimulation (e.g., increasing or upregulating antigen-specific NK cell effector function) and inhibition (e.g., decreasing or downregulating antigen-specific NK cell effector function).

As used herein, the term antigen specific or CXCR6$^+$ "natural killer cell" or "NK cell" refers to the subset of NK cells which are CXCR6$^+$, do not express T cell receptors, and which tend to reside in the liver. As set forth herein, these cells have been shown to be capable of antigen-specific responses.

As used herein, the term "T cell" (i.e., T lymphocyte) refers to those cells which express a T cell receptor; T cells include thymocytes, immature T cells, mature T cells and the like. As used herein the term "B cell" refers to those cells within the B cell lineage, including immature B cells, mature B cells and the like.

As used herein, the term "dendritic cell" refers to a type of antigen-presenting cell which is particularly active in stimulating T cells. Dendritic cells can be obtained by culturing bone-marrow cells in the presence of GM-CSF and selecting those cells that express MHC class II molecules and CD11c. Dendritic cells can also express CD11b$^+$, DEC-205$^+$, CD8-alpha$^+$.

As used herein, the term "antigen-specific NK cell mediated immune response" includes immune responses that are mediated by CXCR6+ NK cells. Such immune responses can be measured by determining antigen specific NK cell effector activity. As used herein, the term "antigen-specific effector activity" or "antigen-specific effector function" includes NK cell effector functions that can be measured after contact with antigen. Exemplary such responses include delayed type hypersensitivity responses, degranulation, cytokine production (e.g., IFN$\gamma$, TNF$\alpha$, IL-12), chemokine production, and/or lysis of target cells. In another embodiment, a more downstream indicator of NK cell effector function, e.g., survival of animals in a model of disease in which antigen specific NK cells are protective can be measured. Exemplary such antigen-specific effector functions can occur after contact with antigen, such as haptens or antigens present on infectious agents. Exemplary assays that can be used to demonstrate antigen-specific NK cell mediated immune responses are set forth in the instant examples.

Chemokine (C—X—C motif) receptor 6 (CD 186/ CXCR6/CXCR6/STRL33), serves in conjunction with CD4 as a co-receptor for infection with human and simian immunodeficiency viruses, and is expressed on subsets of activated cytotoxic T lymphocytes (CTL) and NKT cells, and on a subset of hepatic NK cells. CXCR6 mediates chemotaxis and adhesion of leukocytes to soluble and membrane-anchored. The nucleic acid and protein sequence for human CXCR6 mRNA and protein can be found at Genbank under GI 5730105 and the genomic sequence at GI 224589815. CXCL16, a transmembrane chemokine expressed predominantly in the liver. CXCL16 is the ligand for CXCR6. The nucleic acid and protein sequence for human CXCL16 can be found at GI154816177 and the genomic sequence at GI 224589808.

The term "hapten" refers to a small functional group that corresponds to a single antigenic determinant. Exemplary haptens include organic compounds or mono- or oligosaccharides, or an oligopeptide. These small molecules elicit an immune response only when attached to a large carrier such as a protein.

The term "occupational allergy" includes reactions to antigen exposure at the workplace. Such antigenic stimulus occurs repeatedly and it is generally very difficult to limit exposure to these antigens, sometimes referred to as occupational allergens. Examples of occupational allergies include occupational asthma, occupational rhinitis, and occupational dermatitis (e.g. as experienced by florists, health professionals and repeat hospital patients (to e.g., latex, iodide, formaldehyde), builders (e.g., chromate in cement), hairdressers (e.g., paraphenylenediamine in dyes) and printers (e.g., acrylic dyes)). In one embodiment of the invention, the subject methods can be used to modulate antigen-specific NK cell function in a subject having an occupational allergy.

The term "secondary exposure" includes the second exposure to an antigen, as well as subsequent exposures. In one embodiment of the invention, the subject methods can be used to modulate antigen-specific NK cell function before or after a secondary exposure to antigen.

The term "delayed-type hypersensitivity" refers to hypersensitivity reactions that are not immediate, i.e., take time to develop. Delayed-type hypersensitivity responses are not mediated by IgE antibody-dependent activation of effector cells. Delayed-type hypersensitivity reactions were thought to be mediated by antigen specific T cells, but as set forth herein CXCR6$^+$ NK cells also play a role in these responses. In one embodiment of the invention, the subject methods can be used to modulate antigen-specific NK cell function in a subject having DTH.

In one embodiment, RNAi can be used to downmodulate antigen-specific NK cell mediated effector function, e.g., by downmodulating CXCR6 or CXCL16. RNA interference (RNAi) is a post-transcriptional, targeted gene-silencing technique that uses double-stranded RNA (dsRNA) to degrade messenger RNA (mRNA) containing the same sequence as the dsRNA (Sharp, P.A. and Zamore, P. D. 287, 2431-2432 (2000); Zamore, P. D., et al. *Cell* 101, 25-33 (2000). Tuschl, T. et al. *Genes Dev.* 13, 3191-3197, (1999); Cottrell T R, and Doering T L. 2003. Trends Microbiol. 11:37-43; Bushman F. 2003. Mol Therapy. 7:9-10; McManus M T and Sharp P A. 2002. Nat Rev Genet. 3:737-47). The process occurs when an endogenous ribonuclease cleaves the longer dsRNA into shorter, e.g., 21- or 22-nucleotide-long RNAs, termed small interfering RNAs or siRNAs. The smaller RNA segments then mediate the degradation of the target mRNA. Kits for synthesis of RNAi are commercially available from, e.g. New England Biolabs, Abnova, or Ambion. In one embodiment one or more of the chemistries known in the art for use in antisense RNA can be employed in molecules that mediate RNAi.

The term "interact" as used herein is meant to include detectable interactions between molecules. The term interact is also meant to include "binding" interactions between molecules.

The term "agent" or "compound" or "test compound" includes reagents or test agents which are employed in the methods or assays or present in the compositions of the invention. The term "agent" or "compound" or "test compound" includes compounds that have not previously been identified as, or recognized to be, a modulator of CXCR6 or CXCL16 expression or activity. In one embodiment, more than one compound, e.g., a plurality of compounds, can be tested at the same time in a screening assay for their ability to modulate expression and/or activity of CXCR6 or CXCL16. The term "library of test compounds" refers to a panel comprising a multiplicity of test compounds.

The term "small molecule" is a term of art and includes molecules that are less than about 1000 molecular weight or less than about 500 molecular weight. In one embodiment, small molecules do not exclusively comprise peptide bonds. In another embodiment, small molecules are not oligomeric. Exemplary small molecule compounds which can be screened for activity include, but are not limited to, peptides, peptidomimetics, nucleic acids, carbohydrates, small organic molecules (e.g., polyketides) (Cane et al. 1998. Science 282:63), and natural product extract libraries. In another embodiment, the compounds are small, organic non-peptidic compounds. In a further embodiment, a small molecule is not biosynthetic.

As used herein, the term "test compound" includes a compound that has not previously been identified as, or recognized to be, a modulator of CXCR6 or CXCL16 activity. The term "library of test compounds" is intended to refer to a panel comprising a multiplicity of test compounds. In one embodiment, test compounds may be in dendrimeric or nanoparticulate form for testing in the claimed assays.

As used herein, the term "reporter gene" refers to a gene that expresses a detectable gene product, e.g., RNA or protein. Preferred reporter genes are those that are readily detectable. The reporter gene may also be included in a construct in the form of a fusion gene with a gene that includes desired transcriptional regulatory sequences or exhibits other desirable properties. Examples of reporter genes include, but are not limited to CAT (chloramphenicol acetyl transferase) (Alton and Vapnek (1979), Nature 282: 864-869) luciferase, and other enzyme detection systems, such as beta-galactosidase; firefly luciferase (deWet et al. (1987), Mol. Cell. Biol. 7:725-737); bacterial luciferase (Engebrecht and Silverman (1984), PNAS 1: 4154-4158; Baldwin et al. (1984), Biochemistry 23: 3663-3667); alkaline phosphatase (Toh et al. (1989) Eur. J. Biochem. 182: 231-238, Hall et al. (1983) J. Mol. Appl. Gen. 2: 101), human placental secreted alkaline phosphatase (Cullen and Malim (1992) Methods in Enzymol. 216:362-368) and green fluorescent protein (U.S. Pat. No. 5,491,084; WO 96/23898).

As used herein, the term "indicator composition" refers to a composition that includes CXCR6, for example, a cell that naturally expresses the protein, a cell that has been engineered to express the protein by introducing an expression vector encoding the protein into the cell, or a cell free composition that contains the protein (e.g., purified naturally-occurring protein or recombinantly-engineered protein) that is used in an assay to identify potential modulators of CXCR6 activity.

As used herein, the term upmodulatory composition includes those agents which upmodute the effector function of antigen-specific CXCR6+ NK cells. Similarly, the term downmodulatory composition includes those agents that downmodulate the effector function of antigen-specific NK cells. Exemplary upmodulatory agents include antigens, "agonists" of CXCR6 (which transduces an activating signal via the CXCR6 receptor, such as CXCL16, variants thereof, or nucleic acid molecules encoding CXCL16 or variants thereof), an agent that upmodulates the interaction of CXCR6 and CXCL16, an agent that upmodulates the expression of CXCR6 and/or CXCL16 (e.g., nucleic acid molecules encoding CXCR6 and/or CXCL16) or an agent that otherwise upmodulates survival or function of CXCR6+ NK cells (e.g., an agent that induces signaling via a stimulatory receptor present on antigen specific NK cells, agents that stimulate toll-like receptors, cytokines, or agents that boost NK cell memory) in an effective amount such that antigen-specific NK cell effector function is modulated. Similarly, as used herein, the term downmodulatory agents includes those agents which downmodute the effector function of antigen-specific CXCR6+ NK cells. Exemplary downmodulatory agents include antigens, "antagonists" of CXCR6 (which block a signal via the CXCR6 receptor, e.g., by blocking interaction with the ligand, CXCL16, such as blocking antibodies or soluble forms of CXCR6 (e.g., molecules comprising a CXCR6 extracellular domain)), an agent that downmodulates the interaction of CXCR6 and CXCL16, an agent that downmodulates the expression of CXCR6 and/or CXCL16 (e.g., by mediating RNAi) or an agent that otherwise downmodulates survival or function of CXCR6+ NK cells (e.g., an agent that induces signaling via an inhibitory receptor present on antigen specific NK cells) in an effective amount such that antigen-specific NK cell effector function is downmodulated.

II. Modulating Agents of the Invention

The identification of CXCR6+ NK cells as being capable of mounting antigen-specific responses and the identification of CXCR6 as being required for the function of antigen-specific NK cells, enables the use of agents that modulate NK cell numbers and/or function, e.g., the use of agents that modulate CXCR6 to modulate the effector function of those NK cells. For example, enhancing CXCR6 stimulation enhances antigen-specific NK cell effector function, whereas reducing CXCR6 stimulation reduces antigen-specific NK cell effector function. Exemplary agents that can be used to modulate antigen specific NK cell function are known in the art and certain of these are described in more detail below. Other upmodulatory and downmodulatory agents (e.g., which do not work directly on CXCR6 or CXCL16 yet which modulate the function and/or survival of antigen-specific CXCR6+ NK cells are known in the art and some are described throughout the specification).

A. Downmodulatory Agents

1. Antibodies

In one embodiment, antibodies which bind to CXCR6 or bind to CXCL16 and reduce CXCR6 stimulation, e.g., which block the binding of CXCR6 to CXCL16, can be used to reduce CXCR6 stimulation. Such antibodies can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. The term "antibody" as used herein also encompasses functional fragments of antibodies (i.e., antigen binding fragments), including fragments of chimeric, human, humanized, primatized, veneered or single chain antibodies. Functional fragments include antigen-binding fragments of antibodies which bind to a mammalian CXCR6, and antigen-binding fragments of antibodies which bind to a mammalian CXCL16. For example, antibody fragments capable of binding to a mammalian CXCR6 or CXCL16 or portions thereof, including, but not limited to Fv, Fab, Fab' and F(ab') 2 fragments can be used in the claimed methods. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons has been introduced upstream of the natural stop site or by other routine antibody engineering methods known to those of skill in the art.

Methods of making single chain antibodies, and chimeric, humanized or primatized (CDR-grafted), or veneered antibodies, as well as chimeric, CDR-grafted or veneered single chain antibodies, comprising portions derived from different species, and the like are well known in the art. The various portions of these antibodies can be joined together chemically by conventional techniques, or can be prepared as a contiguous protein using genetic engineering techniques. For example. nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., BioTechnology, 10: 1455 1460 (1992), regarding primatized antibody, and Ladner et al., U.S. Pat. No. 4,946,778 and Bird, R. E. et al., Science, 242: 423 426 (1988)) regarding single chain antibodies.

Humanized antibodies can be produced using synthetic or recombinant DNA technology using standard methods or other suitable techniques. Nucleic acid (e.g., cDNA) sequences coding for humanized variable regions can also be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851 856 (1993); Daugherty, B. L. et al., Nucleic Acids Res., 19(9). 2471 2476 (1991); and Lewis, A. P. and J. S. Crowe, Gene, 101: 297 302 (1991)). Using these or other suitable methods, variants can also be readily produced. In one embodiment. cloned variable regions can be mutated, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993).

The antibody can be a humanized antibody comprising one or more immunoglobulin chains, said antibody comprising a CDR of nonhuman origin (e.g., one or more CDRs derived from an antibody of nonhuman origin) and a framework region derived from a light and/or heavy chain of human origin (e.g., CDR-grafted antibodies with or without framework changes). In one aspect of this embodiment, the antibody comprises the light chain CDRs (CDR1, CDR2 and CDR3) and heavy chain CDRs (CDR1, CDR2 and CDR3) of a nonhuman immunoglobulin.

In one embodiment, antibodies that bind to CXCR6 can be conjugated to an agent in order to deliver them to CXCR6+ NK cells. In one embodiment, the agent is a label, for example, a radioisotope, an epitope label (tag), an affinity label (e.g., biotin, avidin), a spin label, an enzyme, a fluorescent group or a chemiluminescent group. In another embodiment, the antibody is conjugated to a biologically active molecule (such as a modulator of NK cell activity (e.g., a ligand for an NK cell receptor, a cytokine to which NK cells are responsive, a drug or a toxin)).

In another embodiment, antibodies which bind to CXCR6 that are known in the art (or antibodies which comprise the CDRs of these antibodies) can be used in the claimed invention. Exemplary such antibodies include: mAb 4A 11 made by the hybrodoma cell line deposited with the ATCC under accession number PTA-991; mAb 7A2 made by the hybrodoma cell line deposited with the ATCC under accession number PTA-992; mAb 7F3 can be produced by murine hybrodoma 7F3, made by the hybrodoma cell line deposited with the ATCC under accession number PTA-990. In another embodiment, an antibody that inhibits the interaction of any one or more of these antibodies with CXCR6 (i.e., which binds to the same or a similar epitope) can be used in the methods of the invention.

In another embodiment, the antibody or antigen-binding fragment can bind to a mammalian transmembrane (i.e., cell surface) CXCL16 and modulate signaling through CXCR6. As for CXCR6, such antibodies can be made using techniques well known to those of skill in the art (e.g., as described herein) or can be known. Exemplary antibodies known in the art include: mAb 9B10 made by the hybrodoma cell line deposited with the ATCC under accession number PTA-2628; mAb 10B12 made by the hybrodoma cell line deposited with the ATCC under accession number PTA-2629; mAb SD7 can be produced by murine hybrodoma SD7 made by the hybrodoma cell line deposited with the ATCC under accession number PTA-2630.

In one embodiment, the anti-CXCL16 antibody of the invention is mAb 9B10, mAb 10B12, mAb SD7 or an antigen-binding fragment of any of the foregoing. In another embodiment, the binding of the antibody or antigen-binding fragment to mammalian (e.g., human) CXCL16 can be inhibited by mAb 9B 10, mAb 10B12 or mAb SD7. Such inhibition can be the result of competition for the same or similar epitope or steric interference (e.g., where antibodies bind overlapping epitopes or adjacent epitopes).

In another embodiment, antibodies which are specific for mammalian (e.g., human) CXCR6 or mammalian (e.g., human) CXCL16 can be raised against an appropriate immunogen, such as isolated and/or recombinant human CXCR6 or portions thereof (including synthetic molecules, such as synthetic peptides) or isolated and/or recombinant human CXCL16 or portions thereof (including synthetic molecules, such as synthetic peptides). Antibodies can also be raised by immunizing a suitable host (e.g., mouse) with cells that express CXCR6, such as activated T cells or NK cells, or with cells that express CXCL16, such as CD19+ B lymphocytes, CD14+ monocytes/macrophages, dendritic cells or granulocytes or soluble CXCL16. In addition, cells expressing a recombinant mammalian CXCR6 or CXCL16, such as transfected cells, can be used as immunogens or in a screen for antibody which binds thereto (See e.g., Chuntharapai et al., J. Immunol., 152: 1783 1789 (1994); Chuntharapai et al., U.S. Pat. No. 5,440,021).

Preparation of immunizing antigen, and polyclonal and monoclonal antibody production can be performed using any suitable technique. A variety of methods have been described (see e.g., Kohler et al., Nature, 256: 495 497 (1975) and Eur. J. Immunol. 6: 511 519 (1976); Milstein et al., Nature 266: 550 552 (1977); Koprowski et al., U.S. Pat. No. 4,172,124; Harlow, E. and D. Lane, 1988, Antibodies: A Laboratory Manual, (Cold Spring Harbor Laboratory: Cold Spring Harbor, N.Y.); Current Protocols In Molecular Biology, Vol. 2 (Supplement 97, Summer '94), Ausubel, F. M. et al., Eds., (John Wiley & Sons: New York, N.Y.), Chapter 11, (1991)). Generally, a hybridoma is produced by fusing a suitable immortal cell line (e.g., a myeloma cell line such as SP2/0, P3X63Ag8.653 or a heteromyloma) with antibody-producing cells. Antibody-producing cells can be obtained from the peripheral blood or, preferably the spleen or lymph nodes, of humans or other suitable animals immunized with the antigen of interest. The fused cells (hybridoinas) can be isolated using selective culture conditions, and cloned by limiting dilution. Cells which produce antibodies with the desired specificity can be selected by a suitable assay (e.g., ELISA).

Other suitable methods of producing or isolating antibodies of the requisite specificity (e.g., human antibodies or antigen-binding fragments) can be used, including, for example, methods which select recombinant antibody from a library (e.g., a phage display library). Transgenic animals capable of producing a repertoire of human antibodies (e.g., Xenomouse® (Abgenix, Fremont, Calif.)) can be produced using suitable methods (see e.g., Jakobovits et al., Proc. Natl. Acad. Sci. USA, 90: 2551 2555 (1993); Jakobovits et al., Nature, 362: 255 258 (1993)). Additional methods which are suitable for production of transgenic animals capable of producing a repertoire of human antibodies have been described (e.g., Lonberg et al., U.S. Pat. No. 5,545,806; Surani et al., U.S. Pat. No. 5,545,807; Lonberg et al., WO97/13852).

2. Antisense/RNAi

Another aspect of the invention pertains to isolated nucleic acid molecules that are antisense to the coding strand of a CXCR6 or CXCL16 mRNA or gene. An antisense nucleic acid of the invention can be complementary to an entire CXCR6 or CXCL16 coding strand, or to only a portion thereof. In one embodiment, an antisense nucleic acid molecule is antisense to a coding region of the coding strand of a nucleotide sequence encoding CXCR6 or CXCL16 that is unique. In another embodiment, the antisense nucleic acid molecule is antisense to a noncoding region of the coding strand of a nucleotide sequence encoding CXCR6 or CXCL16 that is unique. In a preferred embodiment, an antisense molecule binds to the 3' untranslated region of the CXCR6 or CXCL16 gene.

Given the coding strand sequences encoding CXCR6 and CXCL16, antisense nucleic acids of the invention can be designed according to the rules of Watson and Crick base pairing. The antisense nucleic acid molecule may be complementary to the entire coding region of CXCR6 or CXCL16 mRNA, or alternatively can be an oligonucleotide which is antisense to only a portion of the coding or noncoding region of CXCR6 and CXCL16mRNA. For example, the antisense oligonucleotide may be complementary to the region surrounding the translation start site of CXCR6 or CXCL16 mRNA. An antisense oligonucleotide can be, for example, about 15, 20, 21, 22, 23, 24, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation.

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for a CXCR6 or CXCL16-encoding nucleic acid can be designed based upon the nucleotide sequence of a CXCR6 or CXCL16-gene disclosed herein. For example, a derivative of a *Tetrahymena* L-19 IVS RNA can be constructed in which the base sequence of the active site is complementary to the base sequence to be cleaved in a CXCR6 or CXCL16-encoding mRNA. See for example Cech et al. U.S. Pat. No. 4,987,071; and Cech et al. U.S. Pat. No. 5,116,742. Alternatively, CXCR6 or CXCL16 mRNA can be used to select a catalytic RNA having a specific ribonuclease activity from a pool of RNA molecules. See for example Bartel, D. and Szostak, J. W. (1993) *Science* 261: 1411-1418.

In another embodiment, RNAi can be used to inhibit CXCR6 or CXCL16 expression. RNA interference (RNAi is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D., et al. *Cell* 101, 25-33 (2000). Tuschl, T. et al. *Genes Dev.* 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. The antisense RNA strand of RNAi can be antisense to at least a portion of the coding region of CXCR6 or CXCL16 or to at least a portion of the 5' or 3' untranslated region of the CXCR6 or CXCL16 gene. In one embodiment, siRNA duplexes are composed of 21-nt sense and 21-nt antisense strands, paired in a manner to have a 2-nt 3' overhang. In one embodiment, siRNA sequences comprise TT in the overhang. The target region can be, e.g., 50 to 100 nt downstream of the start codon, 3'-UTRs may also be targeted. In one embodiment, a 23-nt sequence motif AA(N19)TT (N, any nucleotide) can be searched for and hits with between about 30-70% G/C-content can be selected. If no suitable sequences are found, the search may be extended using the motif NA(N21). SiRNAs are preferably chemically synthesized using appropriately protected ribonucleoside phosphoramidites and a conventional DNA/RNA synthesizer. SiRNAs for CXCR6 and CXCL16 are also available commercially from, e.g., Invitrogen, Abnova, Applied Biosystems, and Sigma Aldrich. In one embodiment one or more of the chemistries known in the art for use in antisense RNA can be employed in SiRNAs. In another embodiment, combinations of more than one SiRNA molecule can be used to optimize RNAi.

B. Upmodulatory Agents

In one embodiment, multivalent antibodies (e.g., in tetravalent form or cross-linked, e.g., on a surface) can be used to transmit a positive signal via CXCR6 and enhance antigen-specific NK cell effector function. Methods for making tetravalent antibodies are known in the art Exemplary upmodulatory antibodies include multivalent forms of the anti-CXCR6 antibodies known in the art. In another embodiment, a novel tetravalent antibody can be made and tested for its ability to upmodulate signaling via CXCR6.

In another embodiment, soluble or membrane bound forms of CXCL16, or nucleic acid molecules encoding them, can be made using standard methods and administered to a subject to stimulate CXCR6 activity in NK cells.

In one embodiment, an agent is a soluble form of CXCL16, e.g., an agent comprising a CXCL16 extracellular domain. In one embodiment, soluble CXCL16 can be modified or derivitized to optimize therapeutic properties. For example, in one embodiment, a CXCL16 molecule may be in the form of a CXCL16 Fc chimera (i.e., an Fc fusion protein). In another embodiment, a soluble CXCL16 molecule can be modified by conjugation to a moiety, e.g., that improves its half-life, such as PEG. In yet another embodiment, a soluble CXCL16 molecule can be incorporated into particles, e.g., micro or nanoparticles using methods known in the art. In still another embodiment, a soluble form of CXCL16 can be formulated to optimize availability, e.g., for slow release.

III. Screening Assays

A. Primary Screening Assays

The invention further provides methods for identifying compounds, i.e., candidate or test compounds or agents (e.g., peptidomimetics, small molecules (e.g., small organic molecules, or other drugs) that directly modulate, e.g., increase or decrease signaling via CXCR6 to thereby modulate antigen-specific NK cell mediated effector function. Modulators of CXCR6 can be known (e.g., antibodies which bind to CXCR6 and transduce a signal, CXCL16, as well as antibodies which inhibit signal transduction via CXCR6 by blocking interaction with CXCL16, antisense CXCR6), or can be identified using the methods described herein.

For example, in one embodiment, molecules which inhibit the generation of a signal via CXCR6 can be identified. In another embodiment, molecules which enhance the generation of a signal via CXCR6 can be identified. Such molecules can be identified in screening assays that employ indicator compositions that can be contacted with agents that transduce a detectable signal via CXCR6 in the presence and absence of a test compound and the ability of the test compound to reduce or enhance the signal measured.

The indicator composition can be a cell that expresses the CXCR6 protein, for example, a cell that naturally expresses or, more preferably, a cell that has been engineered to express the protein by introducing into the cell an expression vector encoding the protein. Preferably, the cell is a mammalian cell, e.g., a human cell and the CXCR6 molecule tested is human in origin. Alternatively, the indicator composition can be a cell-free composition that includes the protein (e.g., a cell extract or a composition that includes, e.g., either purified natural or recombinant protein).

A variety of methods can be used to measure the ability of a compound to modulate CXCR6 activity. CXCR6 is a G-protein coupled receptor. Accordingly, in one embodiment, cells expressing CXCR6 can be contacted with CXCL16 to stimulate the cell and the ability of a compound to reduce or enhance CXCL16 induced GPCR-mediated signaling in the cell can be used to indicate that the test compound is one that reduces or enhances CXCR6 activity in the cell. In one embodiment, the cell is an antigen-specific CXCR6+ NK cell.

Signaling via CXCR6 can be measured in a number of different ways. For example, signaling via CXCR6 has been found to increase NF-κB DNA binding activity, induced κB-driven luciferase activity, and up-regulated tumor necrosis factor-α expression in an NF-κB-dependent manner. However, treatment with pertussis toxin ($G_i$ inhibitor), wortmannin or LY294002 (phosphatidylinositol 3-kinase (PI3K inhibitors)), or Akt inhibitor or overexpression of dominant-negative (dn) PI3Kγ, dnPDK-1, kinase-dead (kd) Akt, kdIKK-β, dnIKK-γ, dnIκB-α, or dnIκB-β significantly attenuates CXCL16-induced NF-κB activation. Furthermore, CXCL16 increases cell-cell adhesion and induced cellular proliferation in an NF-κB-dependent manner. CXCL16-mediated NF-κB activation occurs via heterotrimeric G proteins, PI3K, PDK-1, Akt, and IκB kinase (IKK). CXCL16 induces IκB phosphorylation and degradation. Accordingly, in one embodiment, the ability of a compound to reduce NF-κB activation upon contacting an indicator cell with CXCL16 (e.g., in soluble form or bound to a cell or a surface) can be used to indicate the ability of a compound to reduce CXCR6 signaling.

CXCR6 signaling has also been associated with an increase in p70S6K and eukaryotic initiation factor 4E binding protein 1. Accordingly, in another embodiment, the ability of a compound to reduce the CXCL16-mediated increase in the levels of one or more of these molecules can be tested.

In one embodiment, the chosen parameter can be measured in the presence and absence of the compound and the results compared to an appropriate control.

In another embodiment, in lieu of a direct measurement of the ability of a compound to downmodulate one of these parameters, a measurement of a more downstream parameter can be made, e.g., the ability of a compound to reduce the transcription of a gene that is activated by NF-κB can be made.

Exemplary cell based and cell free assays of the invention are described in more detail below.

i. Cell Based Assays

Indicator compositions of the invention can be a cell that expresses a CXCR6 polypeptide, for example, a cell that naturally expresses endogenous CXCR6 or, more preferably, a cell that has been engineered to express an exogenous CXCR6 polypeptide by introducing into the cell an expression vector encoding the polypeptide.

Functional assays can be used to detect and identify agonists and antagonists of a mammalian CXCR6 receptor.

An agent can be studied in one or more suitable functional assays to determine if said agent can modulate (inhibit (reduce or prevent) or promote) one or more functions of CXCR6. For example, an agent can be tested in an extracellular acidification assay, calcium flux assay, ligand binding assay, chemotaxis assay or assay which monitors degranulation or inflammatory mediator release (see, for example, Hesselgesser et al., J. Biol. Chem. 273(25): 15687 15692 (1998) and WO 98/02151).

In another embodiment, an indicator cell can be transfected with a CXCR6 expression vector, incubated in the presence and in the absence of a test compound, and the effect of the compound on NF-κB activation can be determined.

An agent can also be assessed by monitoring cellular responses induced by active receptor, using suitable cells which express a mammalian CXCR6 or a functional variant thereof. For instance, exocytosis (e.g., degranulation of cells leading to release of one or more enzymes or other granule components, such as esterases (e.g., serine esterases), perforin, and/or granzymes), inflammatory mediator release (such as release of cytokines or chemokines). A variety of functional assays which employ recombinant cells which express a mammalian CXCR6 or functional variant thereof can be employed. For example, assays in which expression of an endogenous or exogenous reporter gene (e.g., .beta.-galactosidase, green fluorescent protein) is induced upon ligand binding to a mammalian CXCR6 or variant expressed by recombinant cells (e.g., recombinant bacteria, recombinant yeast, recombinant mammalian cells) can be used and the ability of a compound to reduce reporter gene expression can be determined.

In one embodiment, an agent that can inhibit or promote a function of CXCR6 is identified by monitoring the release of an enzyme upon degranulation or exocytosis by a cell capable of this function. Cells expressing a mammalian CXCR6 or a functional variant thereof can be maintained in a suitable medium under suitable conditions, and degranulation can be induced. The cells are contacted with an agent to be tested, and enzyme release can be assessed. The release of a mediator into the medium can be detected or measured using a suitable assay, such as an immunological assay, or biochemical assay for enzyme activity.

The medium can be assayed directly, by introducing components of the assay (e.g., an antibody that detects a chemokine or cytokine) into the medium. The assay can also be performed on medium which has been separated from the cells or further processed (e.g., fractionated) prior to assay.

In another embodiment, cells expressing a mammalian CXCR6 or a functional variant thereof are combined with a ligand of CXCR6 (e.g., CXCL16), an agent to be tested is added before, after or simultaneous therewith, and Ca2+ flux (a transient increase in the concentration of intracellular free calcium ions [Ca2+]i) is assessed. Inhibition of ligand-induced Ca2+ flux is indicative that the agent is an inhibitor or antagonist of mammalian CXCR6 function. Calcium mobilization can be monitored using a fluorometric imaging plate reader (FLIPR) (see, for example, Coward, P., et al., Anal. Biochem., 270:242 248 (1999)).

To determine whether a test compound modulates cytokine expression, in vitro transcriptional assays can be performed. To perform such an assay, the full length promoter and enhancer (or portion thereof) of a cytokine can be operably linked to a reporter gene such as chloramphenicol acetyltransferase (CAT) or luciferase and introduced into host cells.

As used interchangeably herein, the terms "operably linked" and "operatively linked" are intended to mean that the nucleotide sequence is linked to a regulatory sequence in a manner which allows expression of the nucleotide sequence in a host cell (or by a cell extract). Regulatory sequences are art-recognized and can be selected to direct expression of the desired polypeptide in an appropriate host cell. The term regulatory sequence is intended to include promoters, enhancers, polyadenylation signals and other expression control elements. Such regulatory sequences are known to those skilled in the art and are described in Goeddel, *Gene Expression Technology: Methods in Enzymology* 185, Academic Press, San Diego, Calif. (1990). It should be understood that the design of the expression vector may depend on such factors as the choice of the host cell to be transfected and/or the type and/or amount of polypeptide desired to be expressed.

A variety of reporter genes are known in the art and are suitable for use in the screening assays of the invention. Examples of suitable reporter genes include those which encode chloramphenicol acetyltransferase, beta-galactosidase, alkaline phosphatase or luciferase. Standard methods for measuring the activity of these gene products are known in the art.

The cells used in the instant assays can be eukaryotic or prokaryotic in origin. For example, in one embodiment, the cell is a bacterial cell. In another embodiment, the cell is a fungal cell, e.g., a yeast cell. In another embodiment, the cell is a vertebrate cell, e.g., an avian or a mammalian cell. In a preferred embodiment, the cell is a human cell.

In one embodiment, the level of expression of the reporter gene in the indicator cell in the presence of the test compound is higher than the level of expression of the reporter gene in the indicator cell in the absence of the test compound and the test compound is identified as a compound that activates signaling via CXCR6. In another embodiment, the level of expression of the reporter gene in the indicator cell in the presence of the test compound is lower than the level of expression of the reporter gene in the indicator cell in the absence of the test compound and the test compound is identified as a compound that inhibits the activity of CXCR6.

ii. Cell-Free Assays

In another embodiment, the indicator composition is a cell free composition. Compounds that specifically modulate CXCR6 activity are identified based on their ability to modulate the interaction of CXCR6 with CXCL16. Suitable assays are known in the art that allow for the detection of protein-protein interactions (e.g., immunoprecipitations, fluorescent polarization or energy transfer, two-hybrid assays and the like). By performing such assays in the presence and absence of test compounds, these assays can be used to identify compounds that modulate (e.g., inhibit or enhance) the interaction of CXCR6 with CXCL16.

In one embodiment, the amount of binding of CXCR6 to CXCL16 in the presence of the test compound is greater than the amount of binding of CXCR6 to CXCL16 in the absence of the test compound, in which case the test compound is identified as a compound that enhances or stabilizes binding of CXCR6. In another embodiment, the amount of binding of the CXCR6 to CXCL16 in the presence of the test compound is less than the amount of binding of the CXCR6 to CXCL16 in the absence of the test compound, in which case the test compound is identified as a compound that inhibits or destabilizes binding of CXCR6.

Binding of the test compound to the CXCR6 polypeptide can be determined either directly or indirectly as described above. Determining the ability of the CXCR6 polypeptide to bind to a test compound can also be accomplished using a technology such as real-time Biomolecular Interaction Analysis (BIA) (Sjolander, S, and Urbaniczky, C. (1991) *Anal. Chem.* 63:2338-2345; Szabo et al. (1995) *Curr. Opin. Struct. Biol.* 5:699-705). As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

Other exemplary assays can monitor complex formation between CXCR6 and ligand (e.g., CXCL16), for example, using time-resolved fluorescence or fluorometric microvolume assay technology (FMAT) (see, for example, Kane, S. A. et al., Anal Biochem., 278(1):29 38 (2000), Degan, P. et al., Mol. Biotechnol, 13(3):215 222 (1999) and Saarinen, K. et al., J. Immunol. Methods, 236(1 2):19 26 (2000) regarding time-resolved fluorescence; Miraglia S. et al., J. Biomol. Screen, 4(4):193 204 (1999), regarding FMAT).

In the methods of the invention for identifying test compounds that modulate an interaction between CXCR6 polypeptide and CXCL16, the full-length CXCR6 polypeptide may be used in the method, or, alternatively, only portions of the CXCR6 may be used. The degree of interaction between CXCR6 polypeptides and CXCL16 can be determined, for example, by labeling one of the polypeptides with a detectable substance (e.g., a radiolabel), isolating the non-labeled polypeptide and quantitating the amount of detectable substance that has become associated with the non-labeled polypeptide. The assay can be used to identify test compounds that either stimulate or inhibit the interaction between the CXCR6 protein and CXCL16. A test compound that stimulates the interaction between the CXCR6 polypeptide and a CXCL16 is identified based upon its ability to increase the degree of interaction between the CXCR6 polypeptide and CXCL16 as compared to the degree of interaction in the absence of the test compound. A test compound that inhibits the interaction between the CXCR6 polypeptide and CXCL16 is identified based upon its ability to decrease the degree of interaction between the CXCR6 polypeptide and CXCL16 as compared to the degree of interaction in the absence of the compound.

In one embodiment, the method of detecting or identifying an agent that binds to a mammalian CXCR6 is a competitive binding assay in which the ability of a test agent to inhibit the binding of a reference agent (e.g., an antibody) is assessed. For example, the reference agent can be labeled with a suitable label as described herein, and the amount of labeled reference agent required to saturate the CXCR6 present in the assay can be determined. A saturating amount of labeled reference agent and various amounts of a test agent can be contacted with a composition comprising a mammalian CXCR6 or functional variant thereof under conditions suitable for binding, and complex formation determined. In this type of assay, a decrease in the amount of complex formed between the labeled reference agent and CXCR6 or functional variant thereof indicates that the test agent binds to CXCR6.

The formation of a complex between the reference agent and CXCR6 or functional variant thereof can be detected or measured directly or indirectly using any suitable method. For example, the reference agent can be labeled with a suitable label and the formation of a complex can be determined by detection of the label. The specificity of the complex can be determined using a suitable control such as excess unlabeled reference agent or label alone. Labels suitable for use in detection of a complex between an agent and a mammalian CXCR6 or functional variant thereof include, for example, a radioisotope, an epitope label (tag), an affinity label (e.g., biotin, avidin), a spin label, an enzyme, a fluorescent group or a chemiluminescent group. When labels are not employed, complex formation can be determined by surface plasmon resonance or other suitable methods.

As described herein, CXCL16 can be expressed as a cell surface protein (i.e., transmembrane protein, integral membrane protein) or in soluble form. Accordingly, compositions which are suitable for use in a binding assay include soluble and membrane preparations which comprise a mammalian cell-surface CXCL16 or functional variant thereof. Such membrane preparations can contain natural (e.g., plasma membrane) or synthetic membranes. Preferably, the membrane preparation is a membrane fraction of a cell that expresses a mammalian cell-surface CXCL16 or functional variant thereof. As CXCL16 can also be isolated as a soluble protein, supernatants isolated from cultures of cells that express soluble CXCL16 are also suitable compositions for use in a binding assay.

In more than one embodiment of the above assay methods of the present invention, it may be desirable to immobilize either CXCR6 or a CXCL16 molecule to facilitate separation of complexed from uncomplexed forms of one or both of the polypeptides, or to accommodate automation of the assay. Binding of a test compound to a CXCR6 polypeptide, or interaction of a CXCR6 polypeptide with a CXCR6 CXCL16 in the presence and absence of a test compound, can be accomplished in any vessel suitable for containing the reactants. Examples of such vessels include microtitre plates, test tubes, and micro-centrifuge tubes. In one embodiment, a fusion protein can be provided which adds a domain that allows one or both of the polypeptides to be bound to a matrix. For example, glutathione-S-transferase/CXCR6 fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target polypeptide or CXCR6 polypeptide, and the mixture incubated under conditions conducive to complex formation (e.g., at physiological conditions for salt and pH). Following incubation, the beads or microtitre plate wells are washed to remove any unbound components, the matrix is immobilized in the case of beads, and complex formation is determined either directly or indirectly, for example, as described above. Alternatively, the complexes can be dissociated from the matrix, and the level of CXCR6 binding or activity determined using standard techniques.

Other techniques for immobilizing polypeptides on matrices can also be used in the screening assays of the invention. For example, either a CXCR6 polypeptide or a CXCL16 target molecule can be immobilized utilizing conjugation of biotin and streptavidin. Biotinylated CXCR6 polypeptide or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies which are reactive with CXCR6 polypeptide or CXCL16 but which do not interfere with binding of the CXCR6 polypeptide to CXCL16 can be derivatized to the wells of the plate, and unbound target or CXCR6 polypeptide is trapped in the wells by antibody conjugation. Methods for detecting such complexes, in addition to those described above for the GST-immobilized complexes, include immunodetection of complexes using antibodies reactive with the CXCR6 polypeptide or CXCL16, as well as enzyme-linked assays which rely on detecting an enzymatic activity associated with the CXCR6 polypeptide or CXCL16.

The binding assays and functional assays described above can be used, alone or in combination with each other or other suitable methods, to detect or identify agents which bind a mammalian CXCR6 protein and/or modulators (antagonists, agonists) of a CXCR6 protein function. The in vitro methods of the present invention can be adapted for high-throughput screening in which large numbers of samples are processed (e.g., in a 96-well format).

B. Secondary Screening Assays

Test compounds that directly or indirectly modulate CXCR6 expression and/or activity, e.g., by one of the variety of methods described herein or using a different screening method known in the art, the selected test compound (or "compound of interest") can then be further evaluated in a secondary screen for their effect on NK cells. In another embodiment, a test compound can be tested for its effect on CXCR6+ NK cell effector function in a primary screen.

For example test compounds can be evaluated by contacting the compound of interest with NK cells either in vivo (e.g., by administering the compound of interest to a subject) or ex vivo (e.g., by isolating cells from the subject and contacting the isolated cells with the compound of interest or, alternatively, by contacting the compound of interest with a cell line) and determining the effect of the compound of interest on the cells, as compared to an appropriate control (such as untreated cells or cells treated with a control compound, or carrier, that does not modulate a biological response). For example, after a test compound is identified in a primary screening assay, it can then be tested to confirm that it modulates antigen-specific NK cell effector function in a secondary screening assay.

For example, in one embodiment, the ability of a test compound identified in a primary screening assay to mediate delayed type hypersensitivity (DTH) in RAG knock out mice can be tested. Mice can be sensitized with hapten and, after an appropriate time, can be challenged with hapten and the effect of the compound on the secondary response can be measured (for example, the right ear could be challenged with hapten and the left ear with hapten plus compound). In another embodiment, the mice could be immunized subcutaneously with virus or viral antigen and, after an appropriate time, challenged (e.g., with viral antigen in one ear and antigen plus compound in the other and the effect of the compound on DTH can be measured). In another embodiment, the mice can be challenged with live virus intranasally and the compound can be administered systemically and the effect of the compound on survival can be determined. Additional exemplary assays that can be used to measure the effects of a compound of interest on NK cell effector function are described in the Examples.

In addition or alternative to measuring the effect of a compound of interest on delayed type hypersensitivity responses, other measures of NK cell effector function can be made. For example, in one embodiment, any one or more of a number of NK cell effector functions, including degranulation, cytokine production (e.g., IFNγ, TNFa, IL-12), chemokine production, and/or lysis of target cells can be measured using methods well known in the art. In another embodiment, a more downstream indicator of NK cell effector function, e.g., survival of animals in a model of disease can be measured.

C. Test Compounds

A variety of test compounds can be evaluated using the screening assays described herein. In certain embodiments, the compounds to be tested can be derived from libraries (i.e., are members of a library of compounds). While the use of libraries of peptides is well established in the art, new techniques have been developed which have allowed the production of mixtures of other compounds, such as benzodiazepines (Bunin et al. (1992). *J. Am. Chem. Soc.* 114: 10987; DeWitt et al. (1993). *Proc. Natl. Acad. Sci. USA* 90:6909) peptoids (Zuckermann. (1994). *J. Med. Chem.* 37:2678) oligocarbamates (Cho et al. (1993). *Science.* 261: 1303-), and hydantoins (DeWitt et al. supra). An approach for the synthesis of molecular libraries of small organic molecules with a diversity of 104-105 as been described (Carell et al. (1994). *Angew. Chem. Int. Ed. Engl.* 33:2059-; Carell et al. (1994) Angew. *Chem. Int. Ed. Engl.* 33:2061-).

The compounds of the present invention can be obtained using any of the numerous approaches in combinatorial library methods known in the art, including: biological libraries; spatially addressable parallel solid phase or solution phase libraries, synthetic library methods requiring deconvolution, the 'one-bead one-compound' library method, and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Compound Des.* 12:145). Other exemplary methods for the synthesis of molecular libraries can be found in the art, for example in: Erb et al. (1994). *Proc. Natl. Acad. Sci. USA* 91:11422-; Norwell et al. (1996) *Immunopharmacology* 33:68-; and in Gallop et al. (1994); *J. Med. Chem.* 37:1233-.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223, 409), spores (Ladner U.S. Pat. No. '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); In still another embodiment, the combinatorial polypeptides are produced from a cDNA library.

Exemplary compounds which can be screened for activity include, but are not limited to, peptides, nucleic acids, carbohydrates, small organic molecules, and natural product extract libraries.

Candidate/test compounds include, for example, 1) peptides such as soluble peptides, including Ig-tailed fusion peptides and members of random peptide libraries (see, e.g., Lam, K. S. et al. (1991) *Nature* 354:82-84; Houghten, R. et al. (1991) *Nature* 354:84-86) and combinatorial chemistry-derived molecular libraries made of D- and/or L-configuration amino acids; 2) phosphopeptides (e.g., members of random and partially degenerate, directed phosphopeptide libraries, see, e.g., Songyang, Z. et al. (1993) *Cell* 72:767-778); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); 4) small organic and inorganic molecules (e.g., molecules obtained from combinatorial and natural product libraries); 5) enzymes (e.g., endoribonucleases, hydrolases, nucleases, proteases, synthatases, isomerases, polymerases, kinases, phosphatases, oxido-reductases and ATPases), and 6) mutant forms or CXCR6 molecules, e.g., dominant negative mutant forms of the molecules.

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Compound Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994) *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner U.S. Pat. No. '409), plasmids (Cull et al. (1992) *Proc Natl Acad Sci USA* 89:1865-1869) or phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222: 301-310; Ladner supra.).

Compounds identified in the subject screening assays can be used in methods of modulating one or more of the biological responses regulated by CXCR6. It will be understood that it may be desirable to formulate such compound (s) as pharmaceutical compositions (described supra) prior to contacting them with cells.

Compounds of interest can also be identified using structure based drug design using techniques known in the art.

The instant invention also pertains to compounds identified in the above assays.

IV. Methods of Use

Yet another aspect of the invention pertains to methods of modulating the activity in an antigen-specific NK cell(s) either in vivo or ex vivo. The modulatory methods of the invention involve contacting a cell(s) of a subject with an agent that modulates antigen-specific NK cell effector function (e.g., one or more of an antigen, an agent that modulates the interaction of CXCR6 and CXCL16, an agent that modulates signaling via CXCR6, an agent that modulates the expression of CXCR6 and/or CXCL16 or an agent that otherwise modulates survival or function of CXCR6+ NK cells (e.g., an agent that modulates signaling via an inhibitory or stimulatory receptor present on antigen specific NK cells) in an effective amount such that antigen-specific NK cell effector function is modulated. Exemplary agents include those that modulate the expression and/or activity of CXCR6 and/or CXCL16.

In one embodiment, the modulatory methods of the invention are performed ex vivo and then the treated cells can be administered to a subject. In another embodiment, the modulatory methods of the invention are performed in vivo, e.g., in a subject having a disorder or condition that would benefit from modulation of antigen-specific NK cell effector function.

As used herein, the term "subject" includes living organisms in which an immune response can be elicited. Preferred subjects are mammals. Particularly preferred subjects are humans. Other examples of subjects include monkeys, dogs, cats, mice, rats cows, horses, goats, sheep as well as other farm and companion animals. Modulation of CXCR6+ NK cell numbers and/or function in humans as well as veterinary applications, provides a means to regulate disorders that would benefit from modulation of antigen-specific NK cell effector function in various disease states and is encompassed by the present invention.

Certain subjects can be selected for treatment with the claimed methods. A subject can be identified in advance of treatment or the step of identifying the subject based on selection criteria disclosed herein may be a step of the treatment method.

In one embodiment, the subject is one that has been identified as having a disease or disorder that would benefit from modulation of antigen-specific NK cell effector function prior to treatment with an upmodulatory agent or downmodulatory agent that modulates antigen-specific NK cell effector function (e.g., an agonist or antagonist of CXCR6). For example, in one embodiment, the subject is identified as one that has low or reduced numbers of antigen-specific NK cells or low or reduced function of antigen-specific NK cells as compared to an appropriate control. In another embodiment, a subject is identified as one that has high or increased numbers of antigen-specific. NK cells or high or increased function of antigen-specific NK cells as compared to an appropriate control. In such a case, the methods of the invention can modulate NK cell numbers or function so that the subject NK cell numbers or function in the subject will normalize or improve.

In another embodiment, the subject is identified as one that has low or reduced T and/or B cell numbers or function as compared to an appropriate control. In such a case, the methods of the invention can increase NK cell numbers or function to compensate for the reduced B and/or T cell low function. In another embodiment, a subject is identified as one that has high or increased T and/or B cell numbers or function as compared to an appropriate control. In such a case, the methods of the invention can reduce NK cell numbers or function to reduce or decrease unwanted antigen specific responses.

In another embodiment, a subject is identified as having a reduction or increase in numbers or function of one or more types of immune cells (e.g., one or more types of white blood cells such as NK cells, antigen-specific NK cells, T, cells, or B cells). In another embodiment, a subject is identified as having a reduction or increase in numbers or function of total immune cells.

For example, in one embodiment, a subject is identified as one that has a reduction in e.g., one or more of NK cells, antigen-specific NK cells, T, cells, or B cells or total immune or white cell numbers or function of at least 10%, at least 20%, at least 30%, at least 40%, at least 50%, at least 60%, at least 70%, at least 80%, or at least 90% as compared to an appropriate control. In another embodiment, a subject is identified as one that has an increase in one or more of NK cells, antigen-specific NK cells, T, cells, or B cells or total immune or white cell numbers or function of at least 10%, at least 20%, at least 30%, at least 40%, at least 50%, at least 60%, at least 70%, at least 80%, or at least 90% as compared to an appropriate control.

In one embodiment, the subject may have a congenital disorder leading to the alteration in white blood cell numbers or function (e.g., common variable immunodeficiency leading to low immune cell function or a congenital disorder leading to unwanted immune responses). In another embodiment, the subject or may have been treated with or exposed to an agent (e.g., an immunosuppressive drug, such as corticosteroids (prednisone, medrol), imuran, methotrexate, cellcept, cytoxan, remicade, rituximab, chemotherapy, irradiation), or may be suffering from an infection (e.g., a chronic infection such as a viral infection (e.g., HIV)) or a disorder that results in altered white blood cell function.

In one embodiment, the subject (e.g., whether having altered white blood cell numbers or function or not) can be screened for antigen-specific NK cell numbers or function prior to being treated using a method of the invention. In one embodiment, a subject treated according to the methods of the invention is tested for antigen-specific NK cell numbers or function after treatment. In another embodiment, a subject is tested both before and after treatment.

In one embodiment, the subject (e.g., whether having normal white blood cell numbers and/or function or altered white blood cell numbers or function) is determined to be a subject that would benefit from increased or decreased antigen-specific NK cell activity because the subject has a particular disease or disorder that would be recognized by one of ordinary skill in the art as benefiting from treatment with an agent that modulates CXCR6+ antigen-specific NK cell function. Exemplary such disorders include diabetes (Ivakine 2006 J. Immunol 176:2976; Hedman 2008; Sordi Blood 2005 106:419); atherosclerosis (Aslanian 2006 Circulation 114:583; Galkina 2007); allergic asthama (Latta 2007 Immunology 121:555); transplant (Bouazzaoui 2009 Genes and Immunity 1-15; Jiang 2005); CNS injury (Kim 2010; Calabresi 2002 J. Neuroimmunology 127:96) Nephritis (Teramoto 2008; Garcia 2007); rheumatoid arthritis (Ruth 2006; van der Von 2005 J. of Leukocyte Biology 87:1029); idiopathic arthritis (Martini 2008); Crohn's disease (Diegelmann 2010 Inflamm Bowel Disease); cancer (Wang 2008 Cancer Res. 68:10367; Meijer 2008 Cancer Res 68:4701; Matsumura 2008; Matsumura 2010; Gutwein 2009; Seidl 2007) HIV/AIDS (Liao 1997; Blaak 2005 J. Virology 1686; Limou 2010 J. Infectious Disease 202:908; Duggal 2002 Genes and Immunity 4:245); chronic inflammation of the liver (Heydtmann 2005 J. Immunol 174:1055; Sato 2005 J. Immunol 174:277); psoriasis (Oh 2009 Dermato-Endocrinology 1:114).

A downmodulatory agent as described herein, such as a blocking antibody that binds to CXCR6 or CXCL16 (or antigen-binding fragment thereof) or a chemical compound that blocks the interaction between CXCR6 and CXCL16 or blocks signaling via CXCR6, or a nucleic acid molecule that reduces the expression of CXCR6 and/or CXCL16 can be administered to a subject as a composition. In another embodiment, an upmodulatory agent as described herein, such as a soluble form of CXCL16 or variant thereof or a nucleic acid molecule encoding CXCL16 or a variant thereof, can be administered as a composition. Such compositions typically comprise the modulatory agent and a pharmaceutically acceptable carrier. As used herein the term "pharmaceutically acceptable carrier" is intended to include solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described herein or using methods known in the art.

The identification of CXCR6 as a key regulator of antigen-specific NK cell effector function as described herein allows for manipulation of NK cell activity in a variety of clinical situations using the modulatory methods of the invention. Modulation of antigen-specific NK cells can be performed in vivo or ex vivo in cells of a subject having any one of numerous diseases or conditions associated with unwanted immune responses. Subjects that would benefit from downmodulation or upmodulation of antigen-specific NK cell effector function can be readily selected by one of ordinary skill in the art, e.g., based on the status of their immune cell function and/or based on the presence of a disease or condition or their propensity to develop a disease or condition.

Some examples of modulation of antigen-specific NK cell activity are set forth below.

A. Reducing Unwanted Immune Responses

In one embodiment, a downmodulatory composition of the invention comprising an agent that downmodulates antigen-specific NK cell effector function (e.g., an agent that downmodulates the interaction of CXCR6 and CCL16, an agent that downmodulates signaling via CXCR6, an agent that downmodulates expression of CXCR6 or CXCL16 or an agent that otherwise downmodulates survival or function of CXCR6+ NK cells (e.g., an agent that modulates signaling via an inhibitory or stimulatory receptor present on antigen specific NK cells) is administered to a subject suffering from an unwanted immune response. Other exemplary agents include aptamers, soluble receptors, non-stimulatory ligands, small molecules that might either work as competitive or allosteric antagonists. Such molecules may be known in the art or may be identified using a screening assay, e.g., as described herein.

In one embodiment, a downmodulatory composition is administered to a subject that suffers from a skin disorder that would benefit from decreased cellular infiltration. Exemplary disorders include: Contact Dermatitis, Sceroderma, Psoriasis vulgaris, Diabetes, Rheumatoid arthritis, and Psoriatic arthritis.

In one embodiment, a downmodulatory composition can be administered to a subject having delayed-type hypersensitivity to decrease antigen-specific NK cell activity. In one embodiment, the antigen to which the subject exhibits the DTH response is a hapten. In another embodiment, the antigen is a protein antigen. In one embodiment, the antagonist is administered to a subject suffering from contact hypersensitivity (CHS) to decrease antigen-specific NK cell activity.

In one embodiment, the antigen is one to which the subject is exposed on a repeated basis in the course of their employment, i.e., an occupational allergen.

In one embodiment, one or more downmodulatory agents is administered to the subject after secondary (or subsequent, i.e., repeat) exposure to the antigen and prior to onset of the DTH reaction. In another embodiment, one or more downmodulatory agents are administered to the subject after secondary (repeat) exposure to the antigen and after onset of the DTH reaction. In another embodiment, one or more downmodulatory agents is administered to the subject prior to secondary (repeat) exposure to the antigen.

In one embodiment, the step of administering is performed more than one time.

In one embodiment, the subject to whom the downmodulatory composition is administered is at risk for developing an autoimmune disorder and the agent is administered prior to development of the disorder. In another embodiment, the treatment is administered to a subject having an autoimmune disorder. In another embodiment, the subject is at risk for developing a disorder characterized by unwanted immune cell activation. In another embodiment, the treatment is administered to a subject having unwanted immune cell activation.

In another embodiment, downmodulatory compositions can be administered to a subject having or at risk for developing diabetes, atherosclerosis, allergic asthma, graft v. host disease, transplantation, cortical injury, nephritis, rheumatoid arthritis, Crohn's disease, certain cancers, chronic inflammation (e.g., of the liver). In another embodiment, downmodulatory compositions can be administered to a subject having or at risk for developing asthma, rhinoconjunctivitis, otitis, rhiosinusitis, urticaria, angioedema, eczema, food allergy, drug allergy, insect allergy, and anaphylaxis.

In one embodiment, downmodulatory compositions are administered to a subject prior to that subject receiving a transplant (e.g., of cells or an organ). In another embodiment, such agents can also be administered after transplantation. In another embodiment, such agents are used to treat an organ prior to procurement or transplantation.

Subjects having other disorders know in the art to be mediated, at least in part, by activation of antigen-specific immune cells can also be administered a downmodulatory composition according to the claimed methods.

In one embodiment (e.g., if a subject does not respond to the extent desired using the CXCR6 antagonist alone), one or more additional agents can be administered to the subject. For example, in a preferred embodiment, the method comprises coadministering an immunosuppressive agent (e.g., a known agent that is currently administered alone to attempt to reduce cell-mediated immune responses, e.g., DTH) that inhibits activation of one or more of T cells, B cells, dendritic cells, and NK cells in conjunction with or as a part of a downmodulatory composition of the invention. In one embodiment, the agents are administered at the same time or substantially simultaneously. In another embodiment, the downmodulatory composition is administered prior to the immunosuppressive agent. In yet another embodiment, the downmodulatory composition is administered after the immunosuppressive agent. In one embodiment, the immunosuppressive agent is a steroid.

In another embodiment, an agent for administration can be targeted to antigen-specific NK cells to thereby reduce their activity. For example, a downmodulatory agent may be conjugated to an NK cell inhibitory agent that binds to and inhibits NK cell activity or that targets the downmodulatory composition to the liver. Exemplary such inhibitory agents include those that bind to and stimulate the activity of inhibitory receptors on NK cells, such as CD85j, CD158z, CD158bz, CD158a, CD158d, CD158e1, CD158k, and NKG2A. In another embodiment, a downmodulatory agent of the invention may be coadministered with an NK cell inhibitory agent.

In yet another embodiment, downmodulatory compositions can be used to diminish deleterious immune responses to infectious agents. For example, rigorous immune response to viral antigens can pose health risks to a subject, for example, as in the case of flu-induced acute lung injury. The instant discovery that antigen specific CXCR6+ NK cells specifically recognize viral antigens allows for the use of downmodulatory agents to diminish antigen-specific NK cell activity in subject having or at risk for developing a deleterious immune response to an infectious agent. In one embodiment, a downmodulatory composition can be used to inhibit a deleterious immune response to a virus, e.g., influenza virus, HBV, HCV, VZV, herpesvirus, HIV1, HIV2.

In connection with any of the above treatment methods, a downmodulatory composition may be administered in conjunction with a general immunosuppressant or another additional agent that is the standard of care currently administered to treat the disorder. The antagonist and the additional agent may be administered at the same time or substantially simultaneously. In another embodiment, the downmodulatory composition is administered prior to the additional agent. In yet another embodiment, the downmodulatory composition is administered after the additional agent. In a preferred embodiment, the administration of the downmodulatory composition allows for administration of a lower dose of the additional agent and, therefore, leads to reduced side effects.

B. Enhancing Desired Immune Responses

In another embodiment, antigen-specific immune responses can be enhanced in a subject that would benefit from increased antigen-specific NK cell effector activity by administering an upmodulatory composition of the invention comprising an agent that upmodulates antigen-specific NK cell effector function (e.g., an agent that upmodulates the interaction of CXCR6 and CCL16, an agent that upmodulates signaling via CXCR6 (e.g., CXCL16 or a variant thereof or nucleic acid molecule encoding CXCL16 or a variant thereof), an agent that upmodulates expression of CXCR6 or CXCL16 or an agent that otherwise upmodulates survival or function of CXCR6+ NK cells (e.g., an agent that modulates signaling via an inhibitory or stimulatory receptor present on antigen specific NK cells).

In one embodiment, an upmodulatory composition of the invention is targeted to CXCR6+ NK cells, e.g., by delivering the composition to the liver or by conjugating the agent to a targeting moiety which targets the upmodulatory agent to the liver. With respect to targeting, in one embodiment, CXCR6 can be used to target antigen-specific NK cells for delivery of an agent that stimulates NK cell effector function. For example, in one embodiment, a cytokine (e.g., IL-12 or IL-15) is conjugated to an anti-CDCR6 antibody or to CXCL16 so that it would be delivered to NK cells expressing CXCR6. In another embodiment, an agent which binds to and stimulates signal transduction via an NK cell activating receptor, e.g., CD158e2, CD158g, CD158b, CD158j, CD158i, or CD94 can be used.

In one embodiment, a subject that would benefit from increased antigen-specific NK cell effector activity is a subject with lowered immune cell numbers and/or function (e.g., T and B cell numbers and/or function) as set forth above. Historically, such subjects are not immunized to protect them from future exposure to infectious agents. However, the finding that CXCR6+ NK cells can mediate antigen-specific memory immune responses in subject lacking B and T cells indicates that antigen specific NK cells can be stimulated in these subjects.

In one embodiment, an upmodulatory agent is administered to a subject having lowered immune cell numbers and/or function as set forth above. In another embodiment, the upmodulatory agent is a vaccine or an antigen (e.g., a composition comprising an antigen that is known in the art to provide protective immune responses in subjects that are not immunocompromised) and the agent administered to an immunocompromised subject in order to stimulate antigen-specific CXCR6+ NK cells. In one embodiment, the vaccine comprises a viral antigen, as, for example in the case of a killed viral vaccine, or a tumor antigen. In one embodiment, the viral antigen is from an RNA virus. In another embodiment, the viral antigen is from a DNA virus. In one embodiment, the antigen is from a virus selected from the group consisting of: influenza virus, hepatitis B virus, hepatitis C virus, Varicella zoster virus, herpesvirus, HIV1, and HIV2. In one embodiment, the antigen is an influenza virus antigen. In another embodiment, the antigen is present on an HIV virus. In one embodiment, the composition comprising an antigen can further comprise one more additional upmodulatory agents (e.g., CXCL16 or a variant thereof).

In another embodiment, the antigen is an antigen present on tumor cells. For example, in one embodiment, a composition comprising an antigen present on the tumor cells is administered to a subject having a tumor (e.g., an immunocompromised subject). In one embodiment, the composition comprising an antigen can further comprise an additional upmodulatory agent, e.g., CXCL16 or a functional variant thereof. In one embodiment, the type of tumor is one in which CXCR6 is demonstrated to have a protective effect.

In another embodiment, a subject (whether immunocompromised or not) is administered an upmodulatory composition comprising an antigen (e.g., a viral, bacterial, parasite, tumor antigen) in combination with an additional agent that stimulates CXCR6+ NK cells.

In one embodiment, a subject being treated with an antigen to enhance CXCR6+ antigen-specific NK cell effector function is further administered CXCL16 or variant thereof or another CXCR6 agonist.

In another embodiment, a subject at risk for developing atherosclerosis is treated with an agonist agent of the invention prior to development of the disease to increase scavenger function.

In another embodiment, a subject at risk for developing an autoimmune disorder is treated with an upmodulatory composition of the invention prior to onset of the disorder to promote tolerance.

In another embodiment, an upmodulatory agent of the invention can be used to enhance antigen-specific NK cell responses in a subject suffering from a viral infection, e.g., a chronic viral infection. In one embodiment, the subject is suffering from an infection of the liver. In another embodiment, the subject is suffering from infection with HIV. In another embodiment, the subject is infected with herpesvirus.

Administration

According to the subject methods, one or more agents which modulate CXCR6 activity on NK cells can be administered to the subject by an appropriate route, either alone or in combination with another drug. An effective amount of an agent (e.g., a molecule which inhibits ligand binding, an anti-CXCR6 antibody or antigen-binding fragment thereof, an anti-CXCL16 antibody or antigen-binding fragment thereof) is administered. An effective amount is an amount sufficient to achieve the desired therapeutic or prophylactic effect, under the conditions of administration, such as an amount sufficient to inhibit the interaction of CXCR6+ NK cell with CXCL16 or to enhance stimulation via CXCL16 in a CXCR6+ NK cell. For example, an effective amount can be an amount that is sufficient for inhibition or promotion of CXCR6 receptor function, and thereby, inhibition or promotion, respectively, of a CXCR6-mediated process (e.g., an inflammatory response). The agents can be administered in a single dose or multiple doses. The dosage can be determined by methods known in the art and is dependent, for example, upon the agent chosen, the subject's age, sensitivity and tolerance to drugs, and overall well-being. Typically, an effective amount can range from about 0.01 mg per day to about 100 mg per day for an adult. Preferably, the dosage ranges from about 1 mg per day to about 100 mg per day or from about 1 mg per day to about 10 mg per day. Antibodies and antigen-binding fragments thereof, such as human, humanized and chimeric antibodies and antigen-binding fragments can often be administered with less frequency than other types of therapeutics. For example, an effective amount of an antibody can range from about 0.01 mg/kg to about 5 or 10 mg/kg administered daily, weekly, biweekly or monthly.

A variety of routes of administration are possible including, for example, oral, dietary, topical, transdermal, rectal, parenteral (e.g., intravenous, intraarterial, intramuscular, subcutaneous, intradermal injection), and inhalation (e.g., intrabronchial, intranasal or oral inhalation, intranasal drops) routes of administration, depending on the agent and disease or condition to be treated. Administration can be local or systemic as indicated. The preferred mode of administration can vary depending upon the particular agent chosen, and the particular condition (e.g., disease) being treated. In one embodiment, such agents are administered such that delivery to CXCR6+ NK cells is optimized (e.g., by using art-recognized methods to target the agent to the liver or to CXCR6+ NK cells).

In one embodiment, the agent can be administered as a neutral compound or as a salt. Salts of compounds containing an amine or other basic group can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Salts of compounds containing a carboxylic acid or other acidic functional group can be prepared by reacting with a suitable base, for example, a hydroxide base. Salts of acidic functional groups contain a countercation such as sodium, potassium and the like.

The agent can be administered to the individual as part of a pharmaceutical composition for modulation of CXCR6 function comprising an inhibitor or promoter of CXCR6 function and a pharmaceutically-acceptable carrier. Formulation will vary according to the route of administration selected (e.g., solution, emulsion, capsule). Suitable pharmaceutical carriers can contain inert ingredients which do not interact with the promoter (agonist) or inhibitor (antagonist) of CXCR6 and/or CXCL16 function. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/mL benzyl alcohol), phosphate-buffered saline (referred to herein as PBS), Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986). For inhalation, the agent can be solubilized and loaded into a suitable dispenser for administration (e.g., an atomizer, nebulizer or pressurized aerosol dispenser).

Furthermore, where the agent is a protein or peptide (e.g., derived from CXCL16), the agent can be administered via in vivo expression of the recombinant protein. In vivo expression can be accomplished via somatic cell expression according to suitable methods (see, e.g., U.S. Pat. No. 5,399,346). In this embodiment, a nucleic acid encoding the protein can be incorporated into a retroviral, adenoviral or other suitable vector (preferably, a replication-deficient infectious vector) for delivery, or can be introduced into a transfected or transformed host cell capable of expressing the protein for delivery. In the latter embodiment, the cells can be implanted (alone or in a barrier device), injected or otherwise introduced in an amount effective to express the protein in a therapeutically-effective amount.

This invention is further illustrated by the following examples, which should not be construed as limiting. The contents of all references, patents and published patent applications cited throughout this application are hereby incorporated by reference. Additionally, all nucleotide and amino acid sequences deposited in public databases referred to herein are also hereby incorporated by reference.

EXAMPLES

The Following Materials and Methods were Used in the Examples

Mice:

Rag1-KO (C57BL/6), RAG-2-KO (Balb/c), Rag$\gamma_c$-dblKO (C57BL/6×C57BL/10 F1), and CXCR6$^{gfp/gfp}$ (C57BL/6) mice, and wild-type mice were purchased from Taconic, Jackson and Charles River laboratories. Rag 2-/- IL2rg-/- (C57BL/6×C57BL/10 F1) were as described (Immunity 2:223 1995). Rag-KO/CXCR6$^{+/gfp}$ mice were generated 'in-house'. Mice were used at 6-12 weeks of age according to the institutional animal committees at Harvard Medical School (Boston, Mass.).

Reagents:

DNFB, DNBS, OXA, Acetone and Methanol were purchased from Sigma-Aldrich. Anti-mCXCR-6 purified rat anti mouse monoclonal IgG$_{2B}$ Clone 221002 and isotype control were purchased from RnD Biosciences. Antibodies specific to murine NK1.1, TCRalpha/beta, TCRgamma/delta, Thy1, CD45, Lamp-1, and CXCR6 were purchased from eBiosciences, BD Parmingen, Biolegend, or RnD Biosciences.

Cell Isolations from Spleen and Liver:

Spleens or Livers were passed through a 40 um mesh filter, and red blood cells lysed using ACK lysis buffer. Lymphocytes were enriched by density gradient centrifugation using Nycodenz (Cederlane Labs) according to manufacturer's protocol. Briefly, spleens, lungs, lymph nodes, bone marrow and livers were cut into small pieces with a sterile scalpel and passed through 40-μm mesh filters. For analysis of skin-infiltrating lymphocytes, mouse ears were collected and then ear sheets were mechanically pulled apart, cut into small pieces with a sterile scalpel, digested with collagenase D (5 mg/ml in 2% (vol/vol) FBS in PBS) and passed through 40-μm mesh filters. Samples were enriched for lymphocytes by density-gradient centrifugation with Nycodenz according to the manufacturer's protocol (Cederlane Labs). For flow cytometry analysis or cell sorting, cells were stained with anti-NK1.1. (PK136; Biolegend), anti-TCRβ (H57597; Pharmingen) and anti-TCRδ (GL-3; Pharmingen) or with anti-CD3 (145-2C11; Biolegend), anti-Thy-1 (30H12; Biolegend), anti-CD45.1 (A20; Pharmingen), anti-CD45.2 (104; Pharmingen) anti-LAMP-1 (1D4B; Pharmingen), anti-CXCR6 (221002; R&D Systems), anti-CXCL16 (142417; R&D Systems), rat IgG2a (54447; R&D Systems) and rat IgG2b (141945; R&D Systems), and samples were acquired on a FACSCanto (BD) and analyzed with FlowJo software. NK cells were identified as CD45+, NK1.1+, CD3- or TCR- and sometimes also Thy-1+ and/or GFP+. A FACSAria (BD) was used for cell sorting with Diva software, and purity was >98% for all experiments.

FACS Analysis and Cell Sorting:

FACS samples were acquired on a BD FACS CANTO and analyzed using FlowJo software. Cell sorting was carried out on a BD FACS ARIA using Diva software, and cell purity for all experiments was >98%.

Hapten-Antigen Ear CHS:

On day 0 and day 1, mice were sensitized on their shaved lower abdomen by skin painting with 50 μl 10.5% DNFB in acetone, or 50 μl 5% OXA in acetone/methanol (1:1). Control mice received solvent only. On day 4, mice were either used as donors for cell sorting, or their right ear was challenged with 24 μl of 0.2% DNFB in acetone, or 20 μl of 1% OXA in acetone/methanol, and the left ear was painted with vehicle. Ear thickness to the first cartilage ridge was measured using a micrometer (Mitutoyo, Japan (No. 193-101). To account for acute hapten-induced irritation, background swelling was measured using naive mice. Sensitization dependent, hapten specific ear swelling=(thickness of hapten ear–thickness of control ear) sensitized mouse–(thickness of hapten ear-thickness of control ear) naïve mouse.

Viral Antigen Ear CHS and DTH:

Rag-KO donor mice are immunized subcutaneously with PBS (control) or 5 ug of viral antigen days 0 and 7. For challenge, 50 μl containing 2 μg viral antigen are injected subcutaneously into one ear and PBS into the control ear. Viral DTH was induced by subcutaneous immunization of Rag1-ag or Rag2-ag mice days 0 and 7 with PBS (control) or 5 μg viral antigen. One month later, mice were either used as donors for adoptive-transfer experiments or challenged subcutaneously with 25 μl PBS containing 2 μg viral antigen into one ear and PBS into the control ear. Ear thickness was, measured every 24 h with a micrometer (193-1011 Mitutoyo). To account for acute hapten- or virus-induced irritation, background swelling was measured in naive mice and sensitization-dependent, antigen-specific ear swelling was calculated as follows: (treated ear thickness–control ear thickness)–background swelling.

Generation of VLPs and Influenza Virus for Live Virus Challenge:

VLPs were generated as described 30,34. *Spodoptera frugiperda* (Sf9) cells were coinfected with recombinant baculovirus expressing the influenza proteins HA and/or M1 or the HIV group antigen and envelope proteins. Culture supernatants were collected 3 d after infection and cleared by low-speed centrifugation (2,000 g for 20 min at 4° C.), then VLPs were concentrated by cross-flow filtration and purified through a 20-30-60% discontinuous sucrose gradient at 100,000 g for 1 h at 4° C. VLP bands were collected, dialyzed against PBS and analyzed by immunoblot. Mouse-adapted influenza strain A/PR/8/34 was grown once in 10-day-old embryonated hen's eggs and was used for live virus challenge. Anesthetized mice were infected intranasally by instillation of 50 μl containing influenza stain A/PR/8/34 in PBS (at various PFU values). Alternatively, 500 PFU of VSV was injected intravenously or 250 PFU of VSV was injected intramuscularly. Control mice received PBS only.

In Vitro Killing and Lamp-1 Upregulation:

NK cells were sorted from hapten-sensitized donors at day 4 and were cultured at various ratios together with a 1:1 mixture of autologous DNBS (dinitrobenzene sulfonic acid)-labeled or MHC class I-deficient B cells and unmodified wild-type control B cells. Target and control cells were distinguished by CFSE (carboxyfluorescein diacetate succinimidyl ester) labeling or by expression of the congenic markers CD45.1 and CD45.2. Then, 12 h after coincubation, the ratio of target cells to control cells was determined by flow cytometry. Specific lysis was calculated as follows: (1−(control/target)input/(control/target)NK-exposed])× 100%, where (control/target)input is the ratio of control cells to target cells in the absence of NK, and (conrol/target)NK-exposed is the ratio of control cells to target cells after exposure to NK cells. For analysis of LAMP-1 upregulation on NK cells, NK cells were cultured together with DNBS-labeled B cells and fluorescein isothiocyanate-conjugated mAb specific for LAMP-1 (10 µg/ml) in the presence or absence of mAb to CXCR6 (10 µg/ml), isotype-matched control antibody, or CXCL1.6 protein, and analyzed by flow cytometry for incorporation of anti-LAMP-1 after 3 h.

DNBS labeling of B cell targets:

Naïve B cells were isolated by negative selection using CD43 magnetic beads (Miltenyi Biotech), and suspended at $10^8$cells/ml in PBS. DNBS in PBS was added to a final concentration of 20 mg/ml, cells incubated 10 min at RT and washed twice with PBS containing 10% bovine serum.

Example 1. Memory NK Cell Responses are Antigen-Specific

Figure 1A:
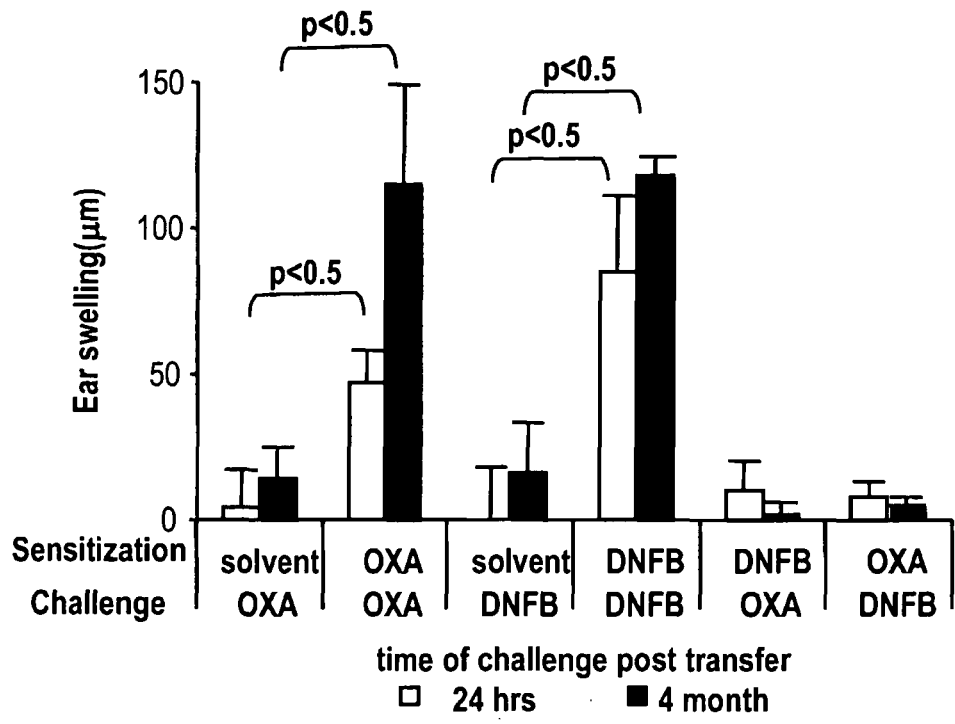
FIG. 1. Memory NK cell responses are antigen specific. a) 100,000 hepatic Thy1$^+$ NK cells were adoptively transferred from naïve or sensitized RAG-KO donor mice into naïve RAGγ$_c$-dblKO recipients, and recipients challenged 24 hrs or 4 month post adoptive transfer with indicated hapten on one ear, solvent on the other ear, and ear swelling determined every 24 hrs using a micrometer. b) Recipient mice were analyzed by FACS 4 month post adoptive transfer and total numbers of NK1.1$^+$ cells determined. Mock recipient RAGγ$_c$-dblKO mice did not present with NK1.1$^+$ cells. c) 100,000 naïve or sensitized, hepatic or splenic Thy1$^+$ NK cells were sorted from donor mice expressing actin under the gfp promoter, and transferred into naïve C57/BL6 mice. Recipient mice were challenged with indicated hapten 6 weeks post adoptive transfer on one ear, and solvent on the other, and ear swelling measured every 24 hrs using a micrometer. d) Recipient mice were analyzed by FACS 6 weeks post adoptive transfer, and total numbers gfp$^+$ NK1.1$^+$ cells determined. Calculation of ear swelling (um): ear thickness (hapten ear-control ear) of mock recipient subtracted from ear thickness (hapten ear-control ear) of NK recipient. a-e The data shown are based on three pooled experiments, 10-15 mice per group total.
Figure 1B:
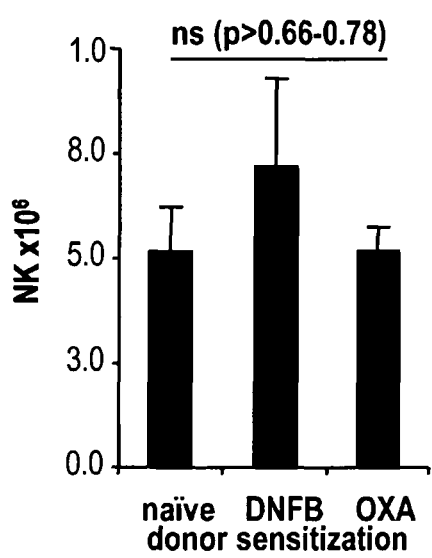
Figure 1C:
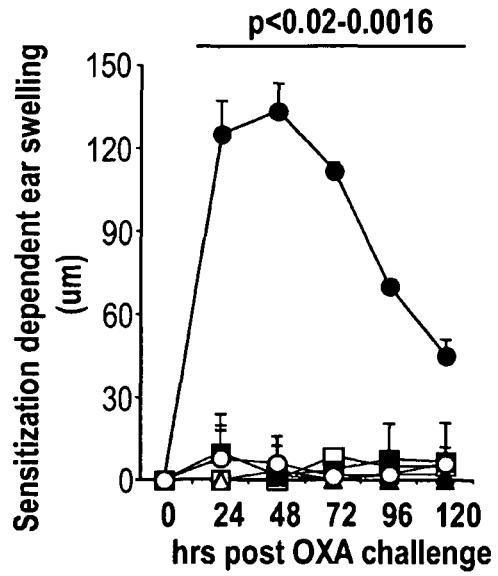
Figure 1D:
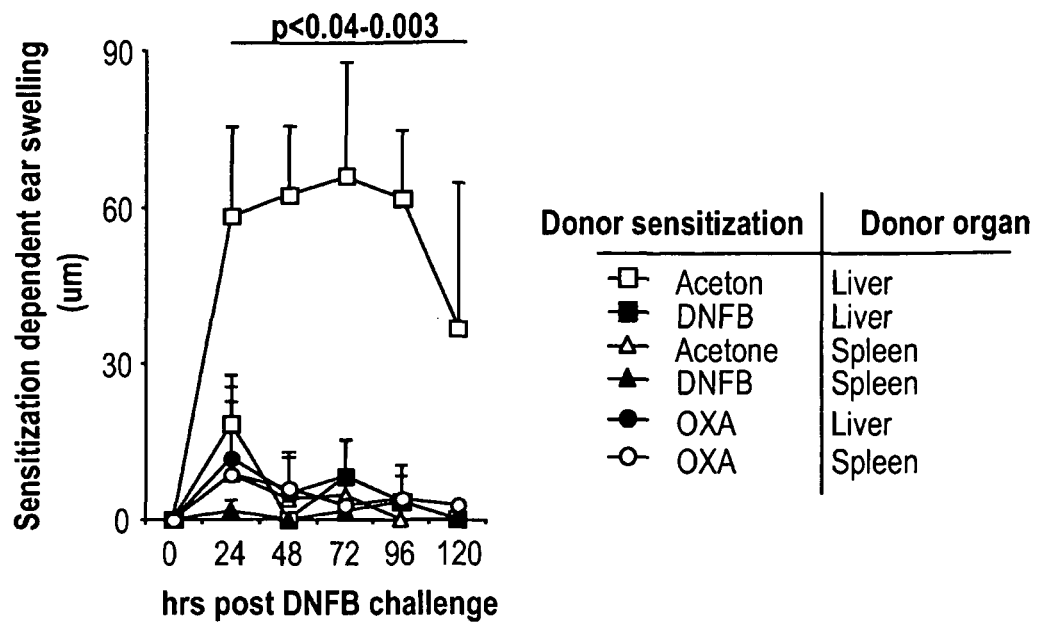
Figure 1E:
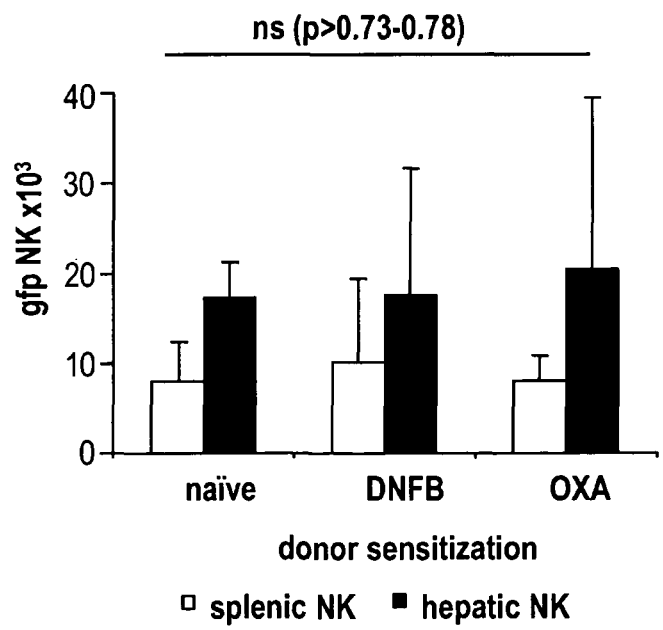

To test if NK cell mediated memory responses are antigen specific, sensitized hepatic Thy-1+ NK cells were adoptively transferred into antigen-free recipients. Rag1-ag (referred to herein as double knock out or DKO) mice were either naive (treated with solvent) or sensitized with DNFB or oxazolone (OXA) and were used as donors for adoptive transfer of flow-cytometry-sorted NK cells into Rag2-agIl2rg-12 recipients; these mice were chosen because this strain cannot produce lymphocytes, including NK cells, allowing for easy recovery and analysis of donor NK cells. Then, 1d or 4 months later, recipients were challenged by painting one ear with hapten and the other with solvent and measured ear swelling after 24 h. Recipients of sensitized hepatic NK cells responded to challenge with same, but not irrelevant hapten-antigen, as demonstrated by significant swelling at site of challenge (FIG. 1a). Thus, NK cell memory is long-lived and antigen specific. In contrast, recipients of naïve hepatic NK did not respond to hapten challenge, confirming that antigen specific NK cell mediated responses are sensitization dependent. All groups of recipient mice harbored similar and expanded numbers of NK cells 4 month post adoptive transfer (FIG. 1b), excluding cell death as a cause for absent CHS responses. To test if long-term survival and NK cell mediated adaptive immunity requires lymphopenia, actin-promotor-driven gfp-positive NK cells were transferred from naïve or sensitized donors into non-gfp wild-type (WT) mice and challenged recipients six weeks post transfer with same or irrelevant hapten-antigen. Concurrent with previous findings, WT recipients of hepatic sensitized NK cells mounted vigorous CHS responses when challenged with same, but not irrelevant hapten-antigen, while recipients of sensitized splenic or naïve NK cells did not respond to challenge (FIG. 1c,d). Similar numbers of gfp$^+$ NK cells were recovered in all recipients six weeks post transfer (FIG. 1e) and also at eight weeks after transfer (the numbers recovered were 24-28% of the original input). Hence, NK cell mediated memory responses to hapten-antigen are sensitization dependent, antigen specific, independent of lymphopenia in the host, and restricted to hepatic NK. In contrast, survival of adoptively transferred NK does not require prior sensitization, is independent of donor organ origin, and does not require lymphopenia in the host. Although the survival and population expansion of adoptively transferred NK cells were independent of prior sensitization or the source organ, only sensitized hepatic NK cells acquired transferable antigen-specific memory, and they did so regardless of the presence of other lymphocytes.

Example 2. Memory NK Cells Accumulate at Effector Sites

Although NK cells are known to require endothelial selectins and $\beta_2$ integrins to access the challenged ears of DNFB-sensitized mice, it has remained unclear whether this recruitment is antigen specific. Thus, NK cells were sorted from naive CD45.1+ donor mice and CD45.2+ donor mice, either wild-type or transgenic for actin promoter-driven GFP expression, that had been sensitized with DNFB or OXA. Mixtures of equal numbers of each population were made and injected these into naive Rag2−/− Il2rg−/− recipient mice. Then, 1 month later, the ears of recipient mice were challenged with hapten and ears and livers were collected at various time points to determine the frequency and genotype of tissue-resident NK cells. Although the livers of recipient mice contained equal numbers of all three donor cell subsets at every time point, infiltrating NK cells in hapten-challenged ears were derived almost exclusively from donors that had been sensitized with the hapten used for challenge (not shown). Thus, only DNFB-sensitized NK cells were recruited to DNFB-challenged ears, whereas OXA-sensitized NK cells 'preferentially' accumulated in OXA-challenged ears. Therefore, not only can memory NK cells discriminate between hapten-based antigens to mediate specific CHS responses but their recruitment and/or retention at sites of challenge is hapten specific.

Example 3 NK Cell Mediated Hapten-Specific CHS Requires CXCR6

Figure 2A:
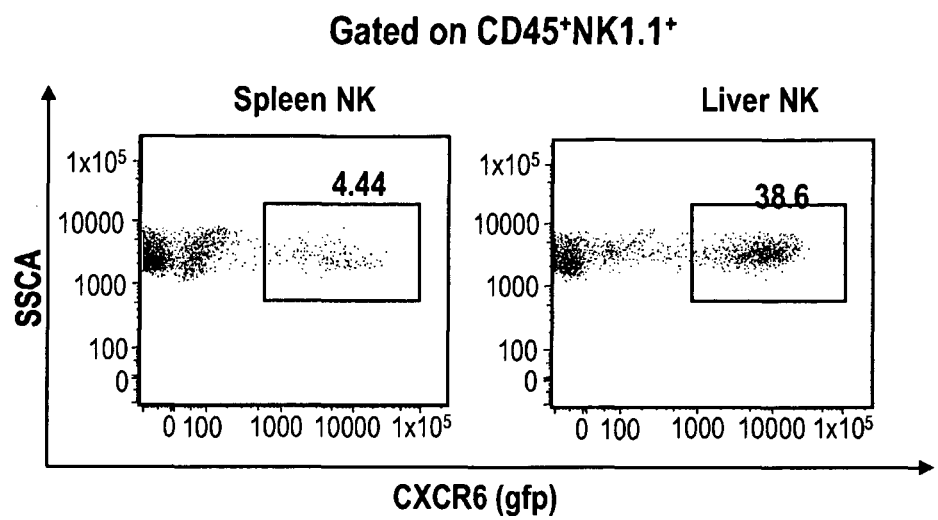
FIG. 2. NK cell mediated hapten-specific CHS requires CXCR6. a,b) Rag-KO mice, in which one allele encoding for the chemokine receptor CXCR6 has been replaced with the gene encoding for green fluorescent protein (gfp), were analyzed for CXCR6/gfp expression using FACS analysis. NK cells are identified as TCRαβγδ-negative NK1.1-positive cells. c,d) 80.000 gfp$^+$ or gfp$^-$ hepatic NK cells from CXCR6/gfp heterozygous mice were sorted from sensitized donor mice and transferred into RAGγ$_c$-dblKO recipients, which were challenged 4 weeks post adoptive transfer with same hapten as sensitization on one ear, and solvent on the other, and ear swelling determined every 24 hrs using a micrometer. e-h) WT (e,g) or Rag-KO (f,h) mice were sensitized with DNFB (e,g) or OXA (f,h) day 0 and 1, injected with 100 ug Clone 221002 or isotype control on day 4, and challenged with indicated hapten on day 5 on one ear, and solvent on the other. Ear swelling was determined every 24 hrs post challenge using a micrometer. Calculation of ear swelling (um): ear thickness (hapten ear-control ear) of solvent control subtracted from ear thickness (hapten ear-control ear) of hapten-sensitized experimental group. The data shown are based on three pooled experiments, 8-12 recipients/mice per group total.
Figure 2B:
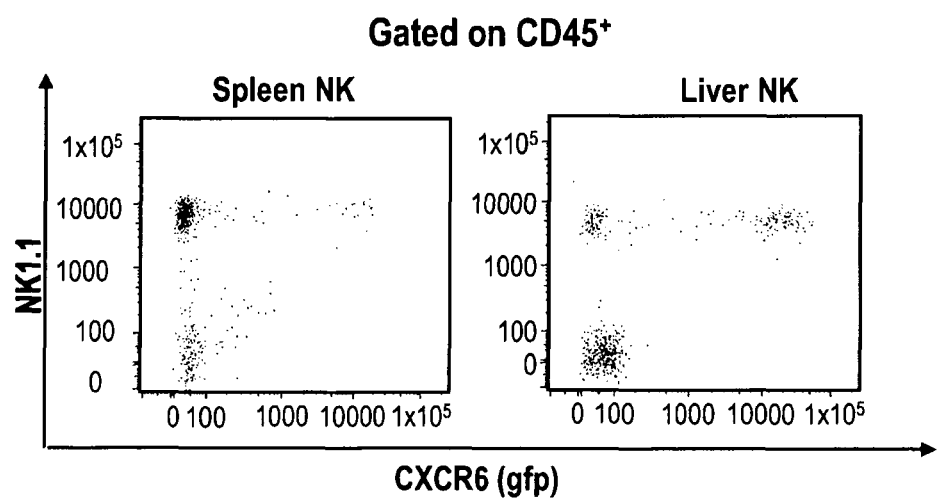
Figure 2C:
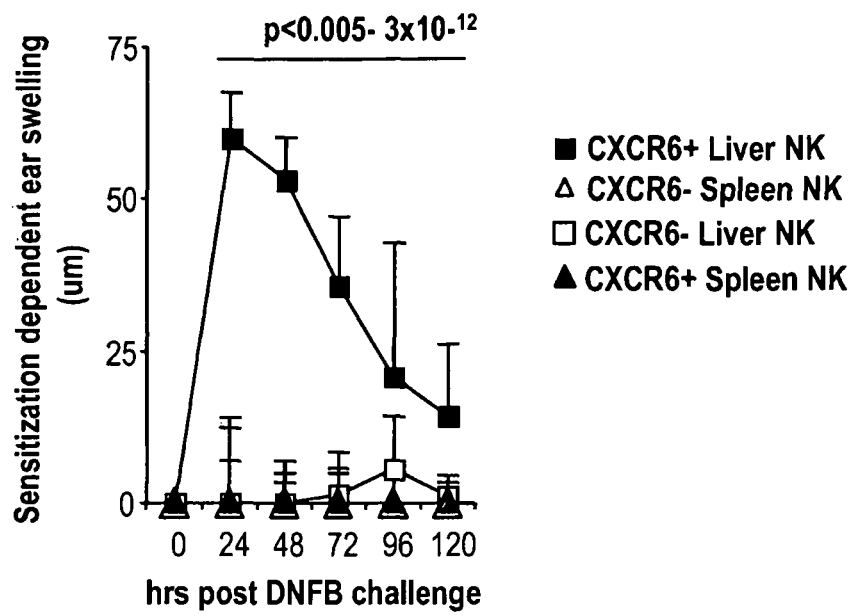
Figure 2D:
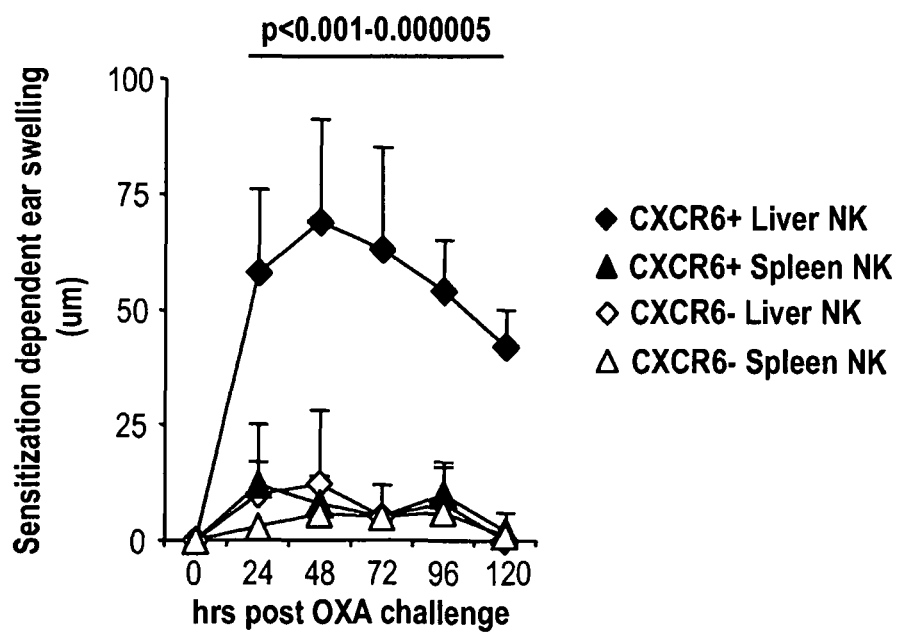

Since NK cell mediated adaptive immunity is restricted to a subset of hepatic NK, receptors uniquely expressed on hepatic NK that may be required for NK cell mediated immune responses were sought. It has previously been demonstrated that CXCR6, a seven-transmembrane g-protein coupled chemokine receptor, is expressed on a subset of hepatic NK, and that it's ligand, CXCL16, is a membrane bound chemokine expressed on hepatic, sinusoidal endothelial cells. However, the biological significance of NK cell expressed CXCR6 is currently unknown. Using mice in which one or both alleles of the gene encoding for CXCR6 are replaced by gfp cDNA, CXCR6 expression was visualized on NK cells. About 40% of hepatic NK, and 5% of splenic NK express CXCR6 in WT (not shown) and Rag-KO mice (FIG. 2a). More importantly, in Rag-KO mice, CXCR6 expression is restricted to a subset of hepatic NK (FIG. 2b).

To assess the role of CXCR6, we explored its contribution to hapten-induced CHS with three complementary approaches: adoptive transfer of sensitized Cxcr6+/− NK cells sorted into CXCR6-expressing (GFP+) and non-CXCR6-expressing (GFP−) subsets; direct sensitization and challenge of wild-type mice and their Rag1−/− Cxcr6−/− and Rag1−/− Cxcr6+/− littermates; and treatment of sensitized wild-type or Rag1−/− mice with antibody to CXCR6 (anti-CXCR6) FIG. 2 and not shown.

Sensitized CXCR6+ hepatic NK cells, but not CXCR6− hepatic NK or splenic NK cells transferred antigen specific CHS responses into naïve hosts, demonstrating that CXCR6 expression on hepatic NK is required for their ability to mediate CHS in viva and that memory NK cells were concentrated in this subset. However, adoptive transfer of GFP+ splenic NK cells failed to mediate CHS, which suggested that CXCR6 expression is insufficient to develop memory. After transfer, GFP+ hepatic NK cells persisted unchanged for at least 6 weeks (not shown), whereas some loss of GFP was noted among GFP+ splenic NK cells, and ~20% of liver-derived GFP-NK cells (but not splenic GFP-NK cells) became GFP+. It is unclear whether this conversion reflected differentiation of mature NK cells or new development from GFP− precursors.

CXCR6+ (gfp+) and CXCR6− (gfp−) NK cells survived equally well in recipient mice (not shown), and splenic NK cells expanded more significantly than hepatic NK, hence inability to mediate CHS is not due to differential survival of these subsets. Expression of CXCR6 (gfp) was fairly stable 6 weeks post adoptive transfer (not shown).

Although CXCR6 alone was apparently insufficient to enable NK cell memory, the results of our adoptive-transfer experiments were consistent with a role for this receptor NK cell-mediated adaptive immunity. Thus, we compared the responsiveness of Cxcr6+/− and Cxcr6−/− mice to DNFB and OXA. CHS responses were much lower but not abolished in Cxcr6−/− mice that had T cells and B cells, whereas Rag1−/− Cxcr6−/− mice were unresponsive to either DNFB (see FIG. 5) or OXA (not shown). Hence, in the absence of T cells and B cells, NK cell-expressed CXCR6 is absolutely required for NK cell-mediated CHS, whereas wild-type mice depend only partially on CXCR6. Because depletion of NK cells in wild-type mice does not result in lower CHS responses, the compromised response in Cxcr6−/− mice probably reflected a combined effect on NK cells and NKT cells.

Figure 2E:
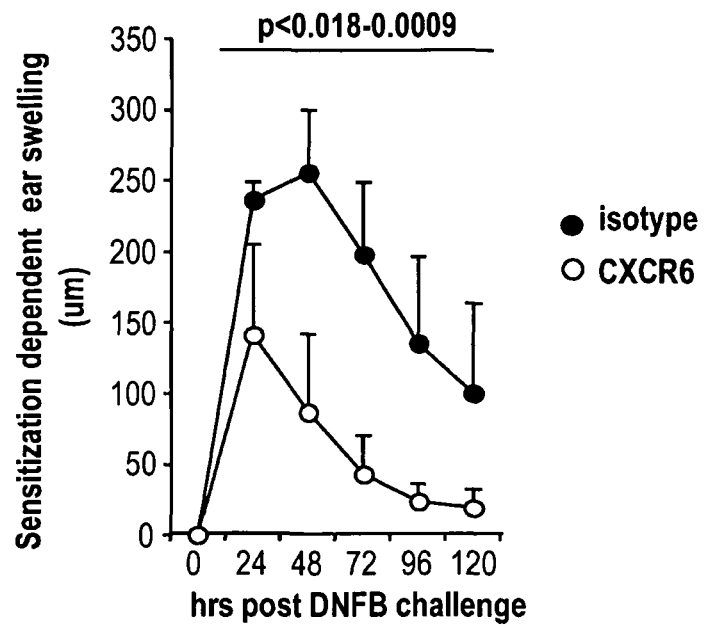
Figure 2F:
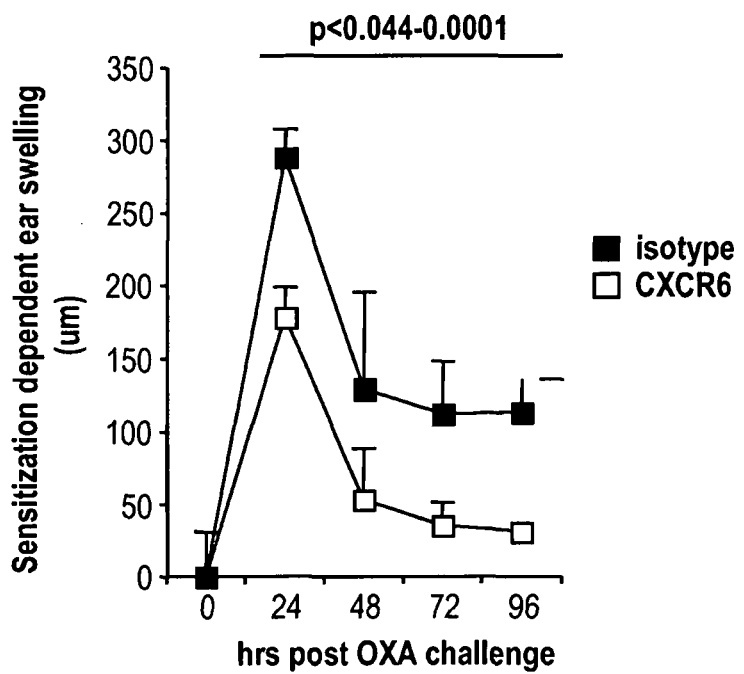
Figure 2G:
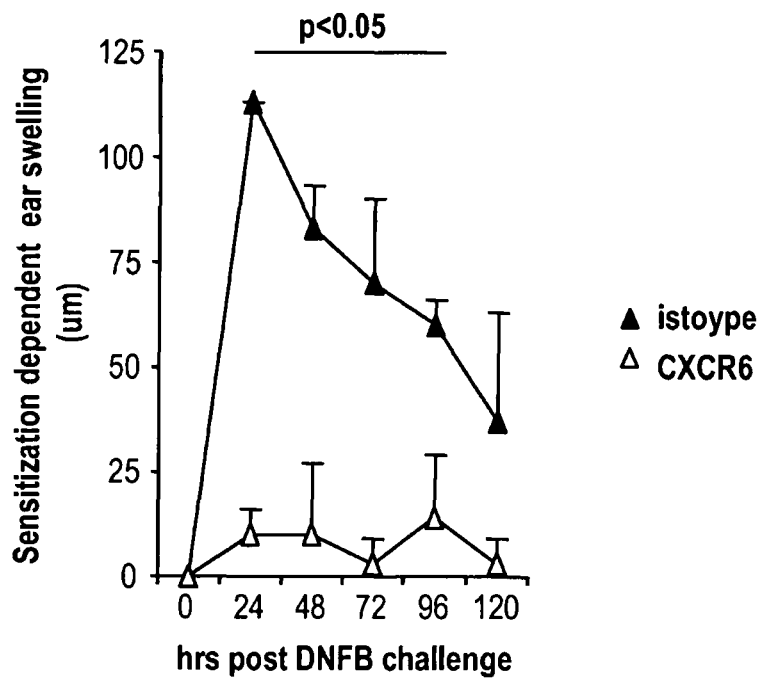
Figure 2H:
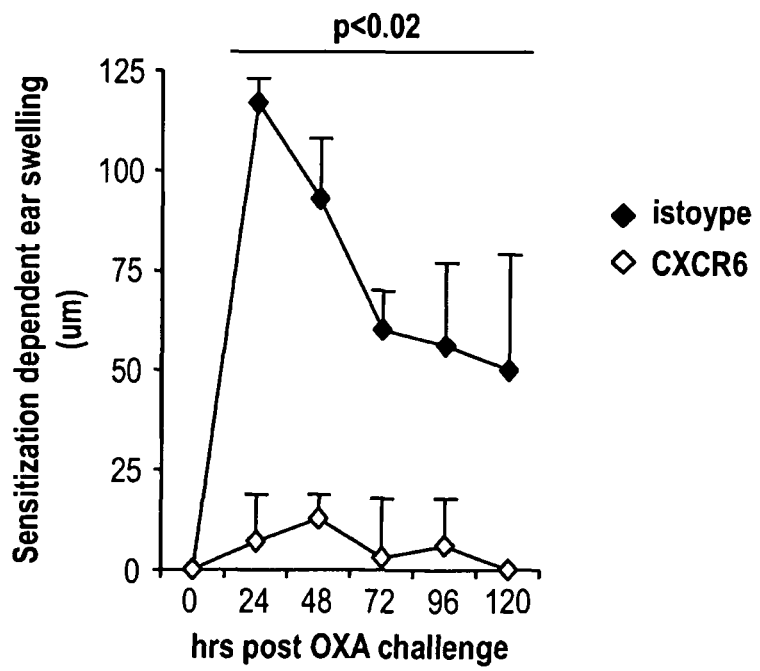

To exclude the possibility that gene targeting of CXCR6 with gfp-cDNA somehow affected the development or effector functions of NK, administration of a monoclonal, non-depleting antibody specific for CXCR6 was tested to see whether it abrogates CHS responses in hapten-sensitized mice. WT or Rag-KO mice were sensitized with DNFB or OXA, and 100 ug anti-CXCR6 or isotype control mAb was administered intravenously 24 hrs before challenge. CXCR6 mAb treated WT mice presented with a significant reduction in CHS responses compared to isotype controls, demonstrating that CHS responses are only partially dependent on CXCR6-expressing cells in WT mice, in which T, NKT, NK and B cells mediate CHS responses (FIG. 2e,f). In contrast, CHS responses were completely abrogated in CXCR6-treated sensitized Rag-KO mice (FIG. 2g,h), in which NK cells are the only mediators of CHS, and CXCR6 expression is restricted to them. Hence, CXCR6 expression on hepatic NK cells is required for hapten-antigen mediated CHS in the absence of T and B cells. This effect of anti-CXCR6 was not due to depletion of NK cells, and short-term treatment with mAb did not result in the relocalization of Cxcr6+/− NK cells to organs other than the liver (not shown). After treatment of wild-type or Rag1−/− mice with anti-CXCR6 or anti-CXCL16, the number of Cxcr6+/− NK cells recovered from various organs was similar to that of mice treated with isotope-matched control mAb.

Example 4. Hapten-Specific Killing is CXCR6 Dependent

Figure 3A:
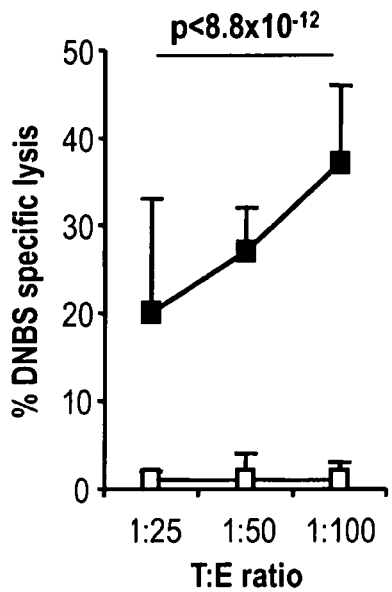
FIG. 3. Hapten-specific killing is CXCR6 dependent. a-d) Sensitized or naive hepatic or splenic NK cells were isolated by cell sorting and mixed in indicated ratios with DNBS labeled B cells (a-c) or MHC-KO B cells (d), and WT control B cells. Target and control cells were distinguished by CFSE or congenic marker and used at 1:1 ratios. 12 hrs post co-incubation with NK cells, ratios of targets:control cells were determined using FACS analysis. Percent specific lysis was calculated as (1-((% control cells/% tartget cells) no NK/(% control cells/% target cells) with NK) x100. (e,f) Donor mice were sensitized with DNFB or OXA days 0, 1, and NK cells sorted 12 hrs post injection from spleen or liver. NK were cocultured with DNBS labeled B cells and 10 ug/ml mAb specific for Lamp-1, in the presence of anti-CXCR6 clone 221002 mAb 10 ug/ml or isotype control. NK cells were FACS analyzed for Lamp-1 incorporation after 3 hrs. Alternatively, sensitized NK cell donor mice were injected with 100 ug/ml anti-CXCR6 clone 221002 mAb or isotype control mAb 12 hrs pre NK isolation. 3-5 independent experiments were pooled; 10-18 donor mice total; 12-20 individual wells per group.
Figure 3B:
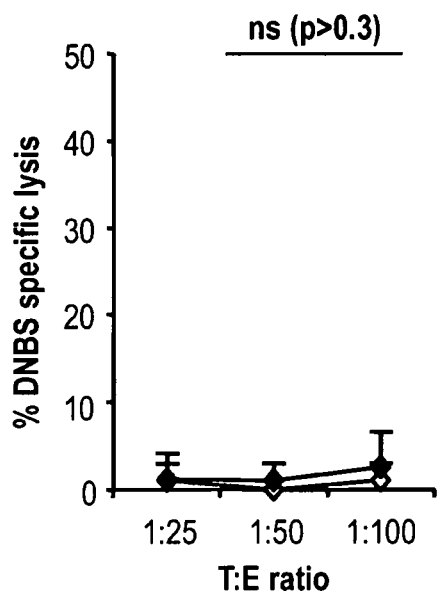
Figure 3C:
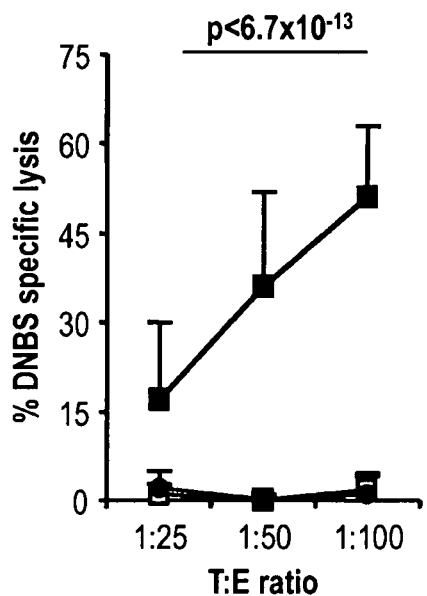
Figure 3D:
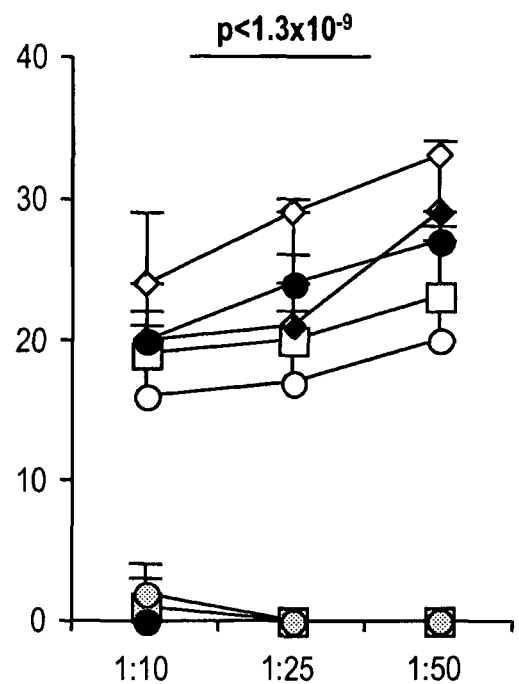
Figure 3E:
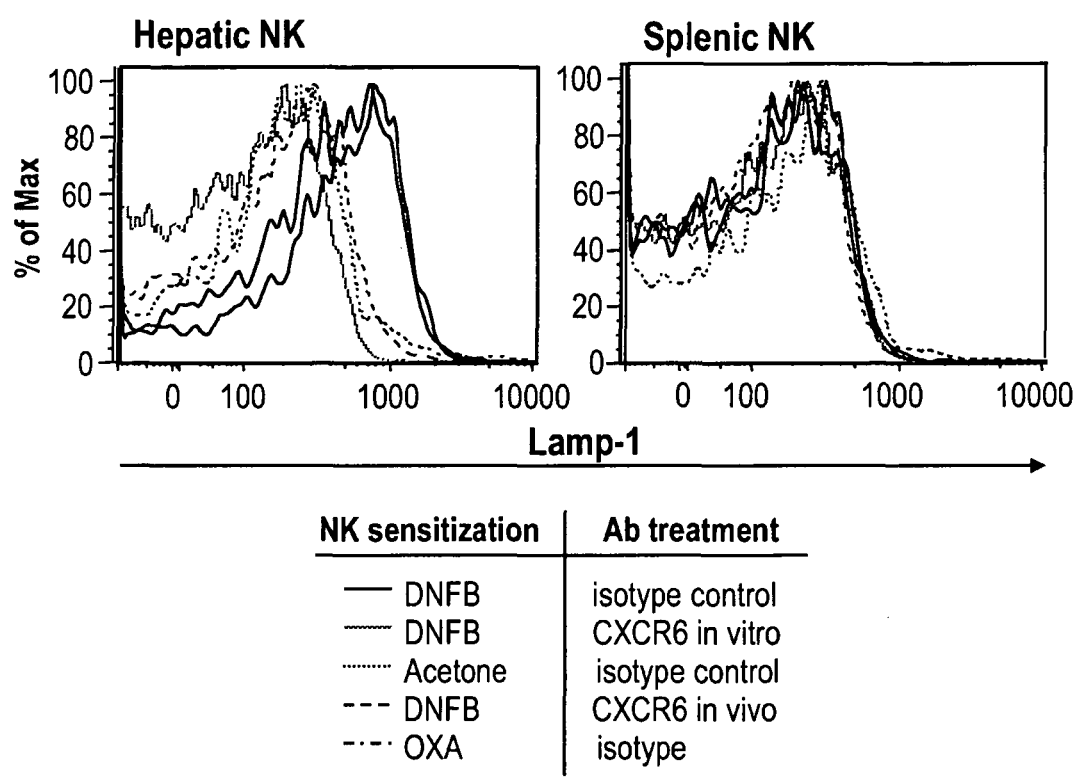

Since killing is one of the hallmarks of NK cell function, whether NK cells are able to kill target cells in a sensitization dependent, hapten-antigen specific manner was tested. Sorted splenic and hepatic NK cells from naïve, OXA and DNFB sensitized donor mice were incubated with DNBS loaded target cells (DNBS is a PBS soluble DNFB analog, allowing haptenization of cells without their fixation) or control cells, and analyzed for antigen specific sensitization dependent killing after 12 hours. Only DNFB sensitized hepatic NK cells killed haptenized targets and did not kill control cells, while naïve NK, DNFB sensitized splenic NK or OXA sensitized hepatic NK cells did not kill hapten-antigen presenting cells or controls (FIG. 3a,b,c). NK cell mediated killing was not generally impaired in NK cells that did not mediate sensitization dependent hapten specific killing, since naïve, DNFB sensitized splenic or OXA sensitized groups of NK cells killed MHC I deficient target cells. (FIG. 3d). Hence, in contrast to the killing of MHC I deficient target cells, hapten specific NK cell mediated killing is sensitization dependent and antigen specific, and mediated only by hepatic NK cells. To visualize sensitization dependent, hapten specific killing on a per cell basis, actively degranulating NK were fluorescently tagged during in vitro killing assays using Lamp-1-specific mAb and flow cytometry. About 10% of DNFB sensitized hepatic NK cells had degranulated during a three hour incubation with DNBS-loaded target cells, while control targets did not induce NK cell degranulation, nor did sensitized splenic or naïve NK degranulate to DNBS loaded target cells (FIG. 3e).

Figure 6B:
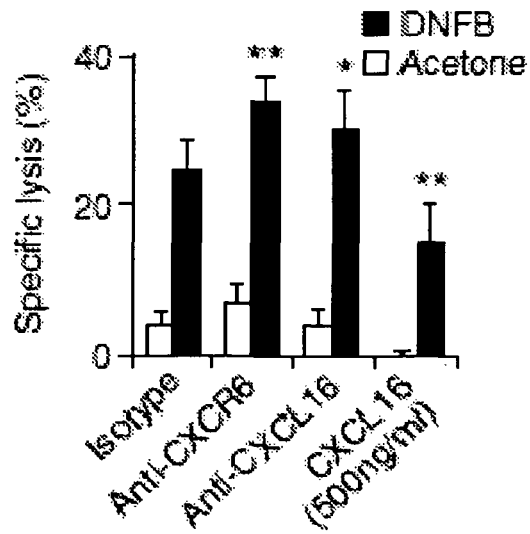

The addition of mAb to CXCR6 to cytotoxicity assays boosted the killing of haptenated B cells by Cxcr6+/− NK cells, especially at suboptimal ratios of target cells to effector cells (FIG. 6b,c). Therefore the NK cell-mediated hapten-specific killing was compared in the presence of blocking mAbs to CXCR6 or CXCL16 or in the presence of recombinant CXCL16 at a target cell/effector cell ratio of 1:25. Blockade of the CXCR6-CXCL16 pathway significantly enhanced the cytotoxicity of sensitized hepatic NK cells, whereas the addition of CXCL1.6 significantly dampened the response (FIG. 6c). Notably, the addition of anti-CXCR6 during the 3 h of in vitro coculture did not affect degranulation, whereas DNFB-sensitized NK cells obtained from mice 12 h after in vivo administration of anti-CXCR6 failed to upregulate LAMP-1. In conclusion, beyond the widespread ability of NK cells to respond to 'missing self' 39, the hepatic memory NK cell subset has the unique ability to also exert cytotoxic activity after encountering MHC class I-sufficient target cells decorated with an antigen to which NK cells were previously sensitized. This adaptive ability seemed to be rapidly lost in vivo when CXCR6 signaling was disrupted, even though CXCR6 was apparently not required for hapten recognition but instead attenuated the cytotoxic effector activity of memory NK cells during the in vitro assay.

Figure 3F:
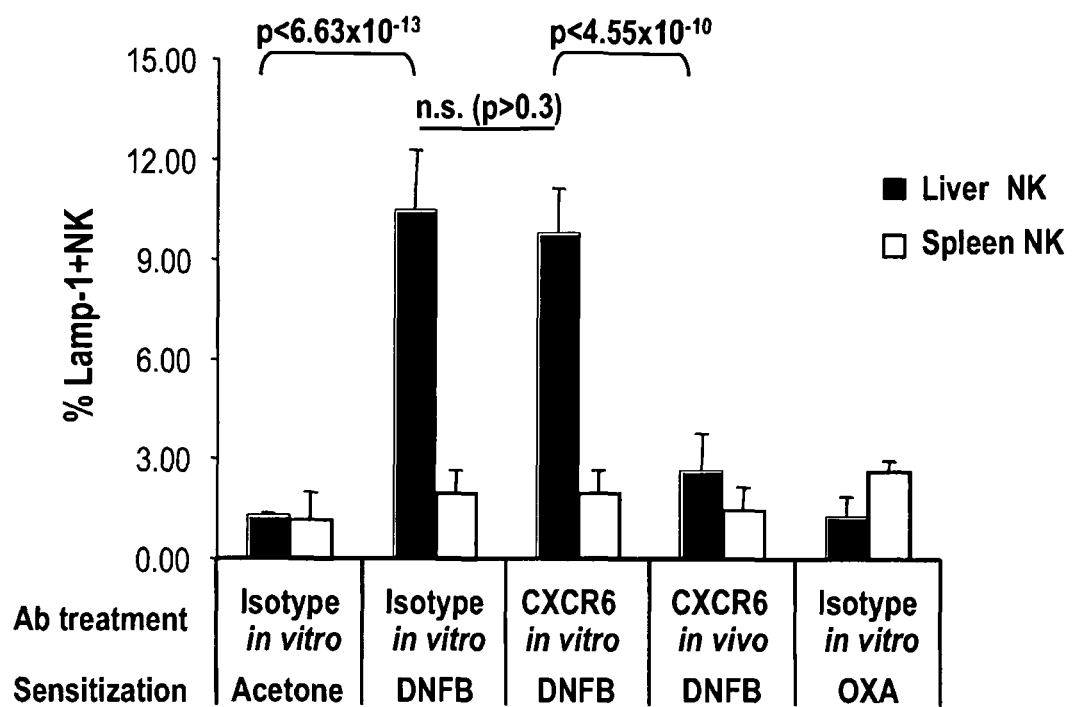

Since NK cell mediated CHS is dependent on CXCR6 expression on NK cells, whether CXCR6-expression on NK is required for sensitization dependent, hapten specific killing was tested. Interestingly, in vivo administration of CXCR6 mAb, but not isotype control, 12 hrs before harvest of NK cells, was sufficient to abrogate Lamp-1 upregulation on sensitized NK stimulated with haptenized target cells, while addition of CXCR6 mAb in vitro during the three hour-long killing/Lamp-1 assay had no effect (FIG. 3f). Splenic NK cells did not kill DNBS loaded target cells regardless of sensitization status or antibody treatment. Hence interference with CXCR6-CXCL16 interactions in vivo abrogates hapten specific killing mediated by sensitized hepatic NK.

Figure 4A:
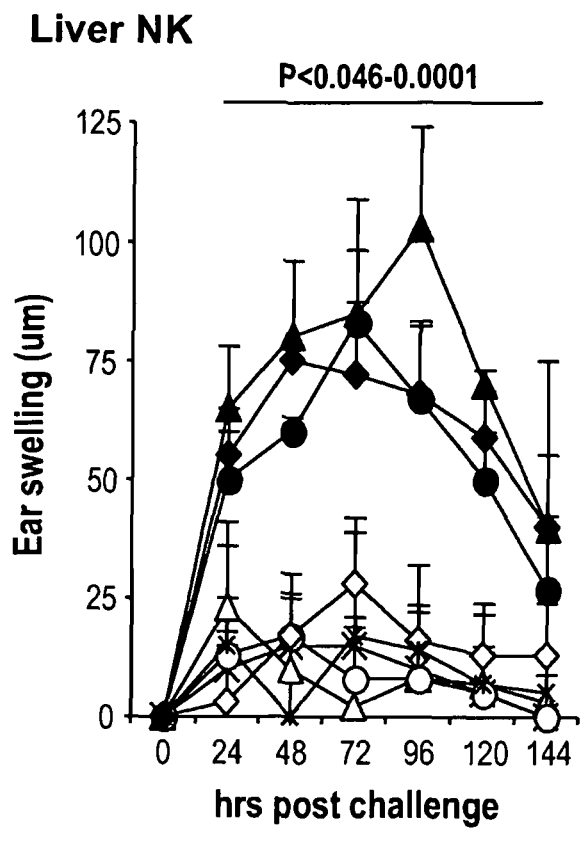
FIG. 4. NK cell memory to viruses and virus like particles is antigen specific. a,b) Rag-KO mice (B6) were immunized subcutaneously with PBS (control), 5 μg UV VSV, or 5 μg Influenza A PR8 or HIV gag/env VLPs days 0 and 7. Four weeks post immunization, 80,000 NK cells from livers (a) and spleens (b) were FACS sorted from immunized donor mice and adoptively transferred into naïve $RAG\gamma_c$-dblKO recipients, which were challenged with 2 μg indicated viral antigen four weeks post transfer. 8-10 recipient mice were analyzed per group. c) Rag-KO donor mice were subcutaneously immunized with PBS (control) or 5 μg Influenza A PR8 VLPs days 0 and 7. Four weeks post immunization, 80,000 NK cells from livers and spleens were FACS sorted from immunized donor mice and adoptively transferred into naïve $RAG\gamma_c$-dblKO recipients. Two months post transfer, $RAG\gamma_c$-dblKO recipients were infected with 2,500 pfu Influenza A PR8 virus intranasally, and their survival determined. 10-19 recipient mice were analyzed per group. Background swelling was determined using naive DKO mice. Sensitization dependent, hapten specific ear swelling= (thickness of viral antigen ear–thickness of control ear) immunized mouse–(thickness of viral antigen ear–thickness of control ear) naïve mouse. d,f,g) Rag-KO mice were immunized days 0 and 7, and challenged day 14 with indicated VLPs, and ear swelling determined every 24 hrs. Twenty-four hours before challenge, mice were injected with 100 ug anti-CXCR6 or isotype control mAb. Background swelling of naïve $RAG\gamma_c$-dblKO control mice was subtracted from corresponding groups to show immunization dependent ear swelling for each individual antigen, and ear swelling calculated as described above. 8-15 mice were analyzed per group e,h) Rag-KO mice were immunized days 0 and 7 with indicated VLPs or PBS, and infected intranasally with 2,500 pfu (e), or 10,000 pfu (h) four weeks post immunization. Twenty-four hours before challenge, mice were injected with 100 ug anti-CXCR6 or isotype control mAb, and, and their survival determined. 8-12 mice were analyzed per group. C57BL/6 Rag-KO donors and C57BL/6xB10F1 $RAG\gamma_c$-dblKO recipient mice were used in a-f, Balb/c Rag-KO mice in g and h.
Figure 4B:
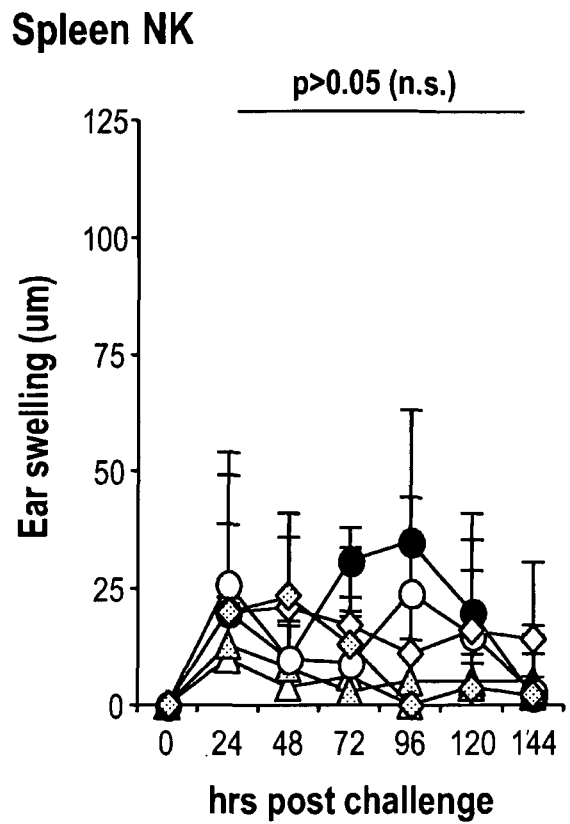

Example 5. NK Cell Memory to Viruses and Virus Like Particles is Antigen Specific NK cell mediated adaptive immune responses may be exploitable for the treatment of infectious diseases, if it can be shown that NK cells mount antigen specific memory responses to infectious pathogens. NK cell mediated responses were examined to three different non-infectious virus like particles (VLPs), Influenza A strain PR8 H1N1 (PR8 VLPs; containing both HA and M1 from influenza strain A/PR/8/34), Influenza A strain PR8 HA-deficient VLPs (M1 VLPs), HIV group antigen /envelope (gag/env) VLPs, and two life viruses capable of lethally infecting mice, Influenza A PR8 (PR8) and Vesicular Stomatits Virus (VSV). Rag-KO mice were immunized with PR8, gag/env VLPs or UV killed VSV (UV VSV), followed by sorting and adoptive transfer of splenic and hepatic NK cells into DKO recipients that were challenged four weeks post transfer with same or irrelevant viral antigen. Concurrent with hapten-antigen-derived data, NK cell mediated CHS responses to viral antigens were sensitization dependent, restricted to hepatic NK, and antigen specific. Specifically, CHS responses were mounted to UV VSV, PR8 and gag/env VLPs, and hepatic NK cells distinguished between PR8 VLPs and UV VSV, and gag/env and PR8 VLPs, while naïve or splenic NK cells did not mediate CHS responses (FIG. 4a,b).

Figure 4C:
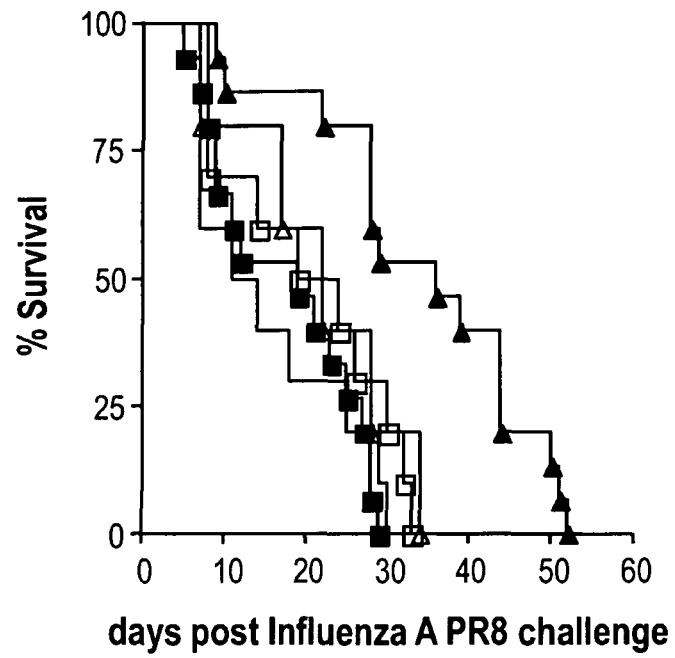

Next, it was determined whether NK cell mediated antiviral memory responses improve the survival of DKO recipients by challenging DKO recipients and naïve DKO control mice with life Influenza A virus three-month post adoptive transfer. Concurrent with viral-antigen mediated CHS data, sensitized hepatic NK cells prolonged the survival of recipient mice significantly (25 days on average) upon lethal Influenza challenge, while naïve or splenic NK did not (FIG. 4c).

When we first used recipients of PR8-VLP-sensitized hepatic NK cells in DTH assays with PR8-VLPs and 2 months later infected the mice with intact virus, we found the magnitude of the DTH-induced ear swelling correlated with the degree of protection against subsequent lethal infection (not shown). Analogous to our findings obtained with haptens, PR8-VLP-sensitized splenic NK cells conferred very low or absent DTH responses and failed to protect against influenza infection, which indicated that memory NK cells are excluded from the spleen regardless of their antigen specificity. Of note, recipients of NK cells purified from lungs of PR8-VLP-sensitized donors also showed a modest DTH response and protection against viral challenge, albeit to a lesser degree than that of recipients of hepatic NK cells; this indicated that some memory NK cells reside in the lungs. Notably, the protection afforded by NK cells was virus specific, as immunization of Rag1-ag mice with two different formulations of influenza VLPs (VLPs containing both HA and M1 (PR8-VLPs) or HA-free VLPs containing M1 (M1-VLPs)) protected vaccinated mice from lethal challenge with influenza but did not protect them from lethal challenge with VSV (FIG. 7). Analogously, Rag1-ag mice immunized with UV-VSV survived longer than PBS-treated controls did after challenge with VSV but not after challenge with influenza.

Although the experiments reported above suggested that NK cells may be likely vaccine targets, all recipients of memory NK cells eventually succumbed to VSV infection (FIG. 7). This could have reflected an inability of memory NK cells to confer sterilizing immunity or the number of memory NK cells may have been insufficient for the relatively high load and systemic dissemination of VSV in our protocol (500 plaque-forming units (PFU) administered intravenously). To distinguish between those possibilities, we monitored the survival of UV-VSV-immunized and naive Rag2-/- BALB/c mice in response to localized infection with the median lethal dose for this strain (250 PFU VSV administered intramuscularly). After challenge with this protocol, nearly all immunized mice survived, whereas about half of the naive mice and mice immunized with non-VSV antigens (such as VLPs containing influenza or HIV) died, as expected (FIG. 7e). Thus, in the absence of T cells and B cells, memory NK cells can provide effective and specific protection against certain viruses, at least when the infectious agent is administered locally and at a moderate dose.

Figure 4D:
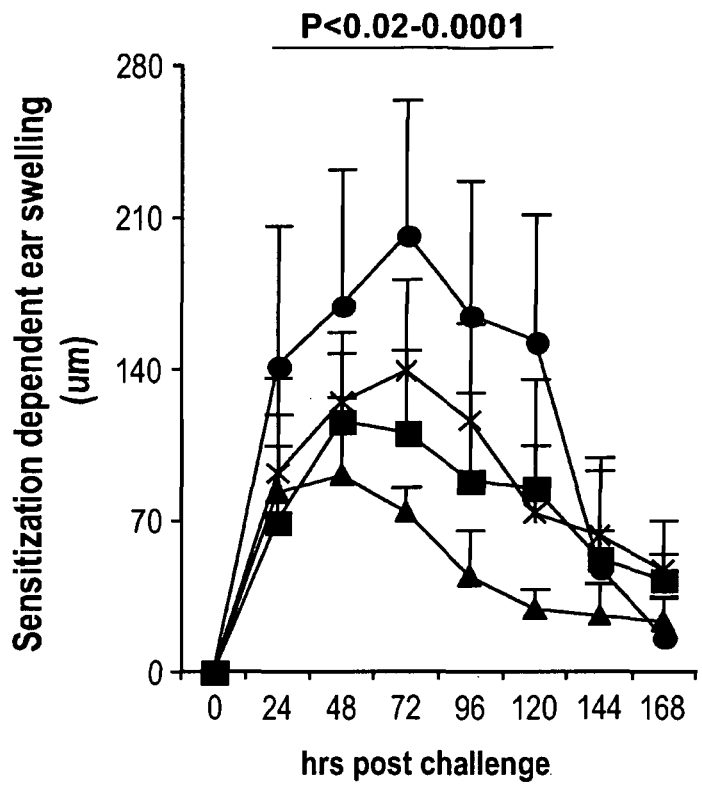
Figure 4E:
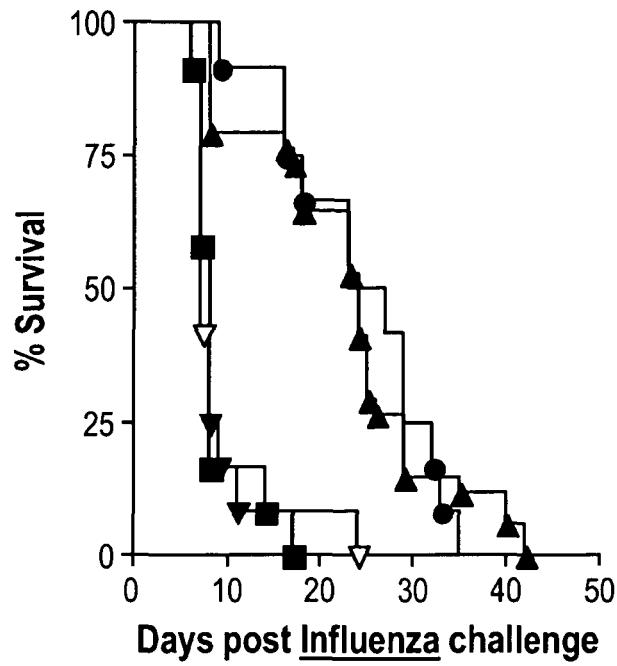

It has previously been shown that Influenza A encoded Hemmagglutinin (HA) is a ligand for the activating receptor Nkp46, which is expressed on all murine (and human) NK cells, and Nkp46-deficiency in mice increases morbidity and mortality significantly upon life virus challenge. In these experiments however, only hepatic, but not splenic PR8 VLP immunized. NK cells enable increased survival of recipient mice upon life influenza challenge. It was possible that Influenza specific memory NK cells may not require HA recognition for their effector function, but recognize Influenza A derived antigens distinct from HA. To test this hypothesis, Rag-KO mice were immunized with either HA-containing PR8 VLPs, or HA-deficient M1 VLPs, and determined CHS responses to same or different VLP. Both HA$^+$ PR8 VLPs and HA" M1 VLPs elicited strong CHS responses in Rag-KO mice, and NK cells cross-reacted to either antigen (FIG. 4d). Importantly, immunization of Rag-KO mice with either VLP significantly equally and significantly prolonged the survival of immunized Rag-KO mice upon lethal challenge (FIG. 4e).

It is highly unlikely that NK cells cross-react to contaminants present in VLP preparations, which are assembled in vitro from viral proteins generated in insect cells, given that immunization with VLPs significantly prolongs survival of immunized mice upon life virus challenge. However, to exclude this possibility entirely, two VLPs that only differ in their protein content were used, PR8 (hemagglutinin/neuromimidase) and HIV (group antigen/envelope) VLPs to immunize and challenge Rag-KO mice, and determined their CHS responses. This experiment also tests whether mouse NK cells can recognize and remember a virus that could not have imposed evolutionary pressure on mice.

Figure 8A:
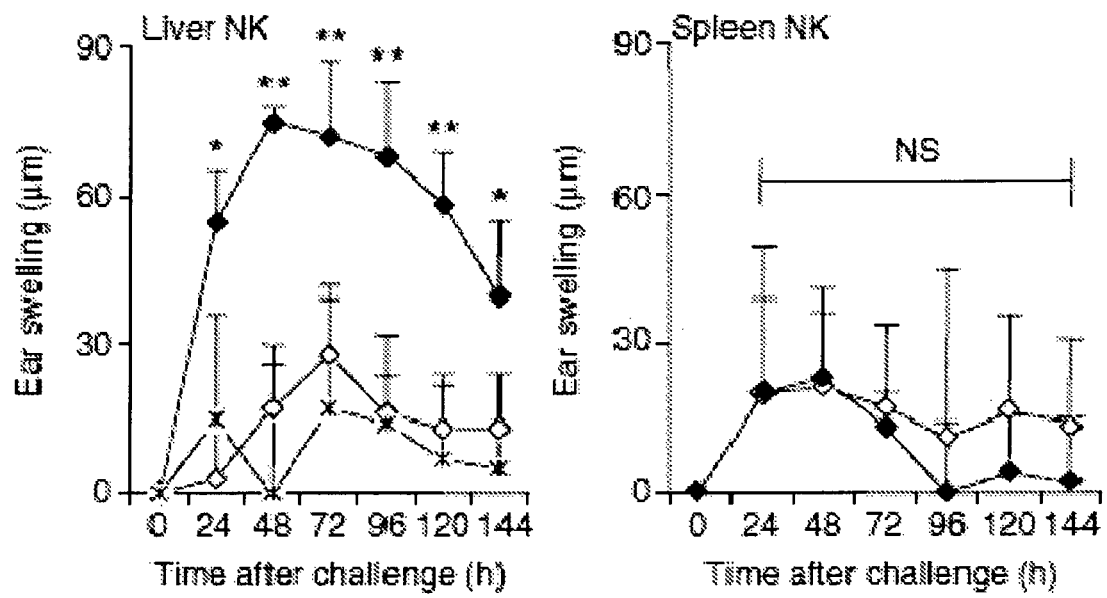
Figure 8B:
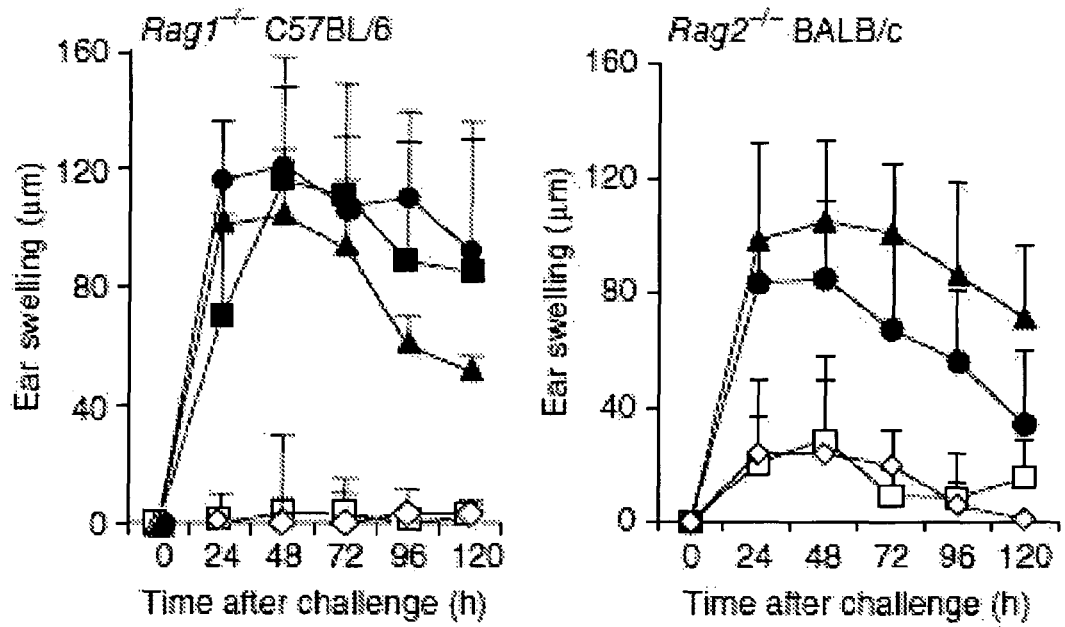

HIV-1 is a lentivirus that causes acquired immunodeficiency syndrome (AIDS) in humans, whereas mice are resistant to HIV-1 infection. One month after sensitizing donor mice with HIV-1-containing VLPs, we transferred splenic or hepatic NK cells into naive Rag2-/- Il2rg-/- recipients and challenged the ears of recipient mice 1 month later by injecting either HIV-1-containing VLPs or PR8-VLPs. Primed hepatic NK cells, but not splenic or naive NK cells, mounted a vigorous recall response to HIV-1 but not to influenza A (FIG. 8a). Moreover, RAG-independent memory of HIV-1 and influenza was inducible in both C57BL/6 and BALB/c mice and was always specific for the virus used during sensitization (FIG. 8b), which indicated that hepatic NK cells can develop specific memory of diverse viral antigens regardless of viral host restrictions or genetic background.

Figure 4F:
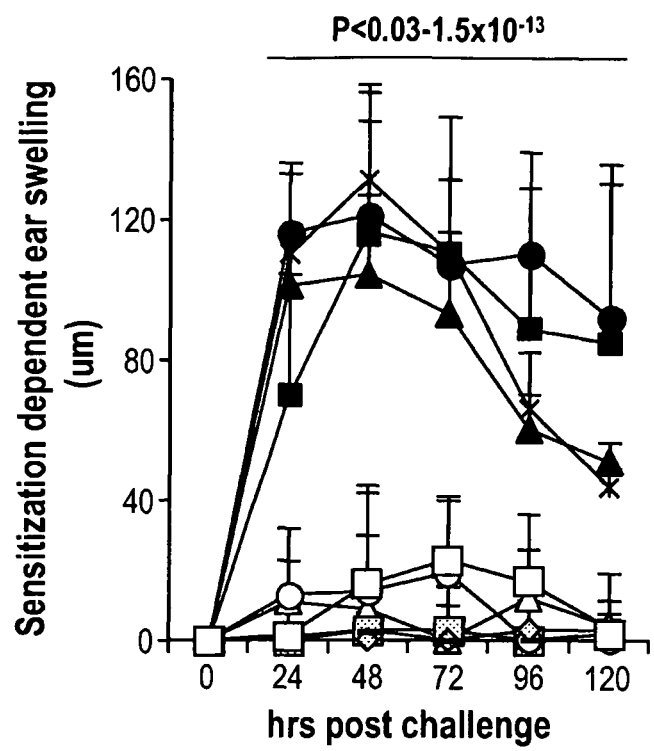
Figure 4G:
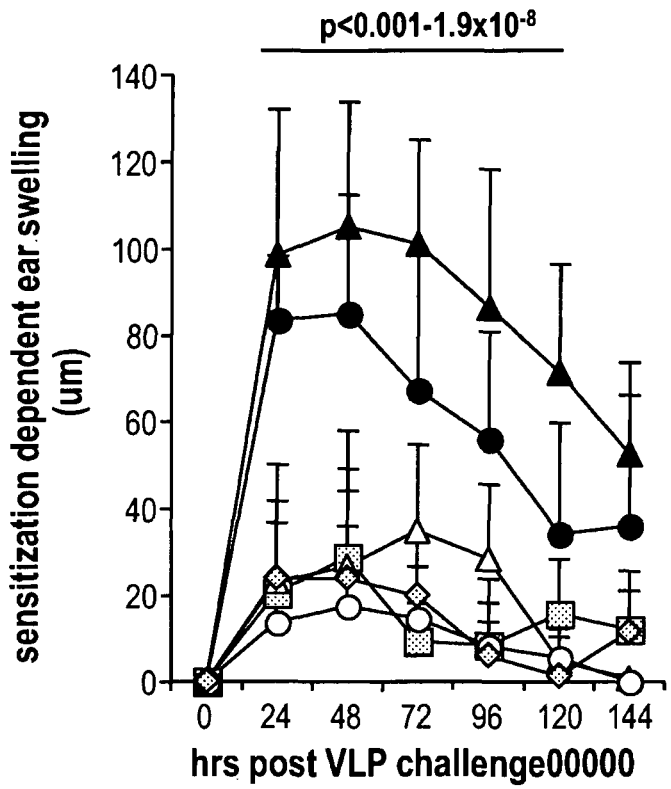
Figure 4H:
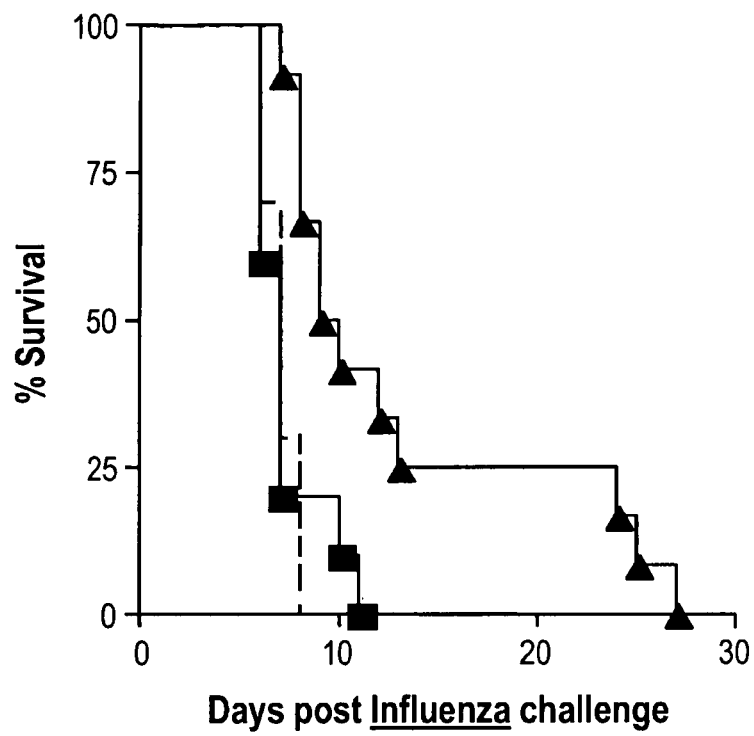

Importantly, both Influenza and HIV VLPs elicited significant CHS responses in Rag-KO mice, and NK cells distinguished Influenza-from HIV-VLP-derived antigen (FIG. 4f). Hence, NK cell mediated CHS responses to Influenza VLPs are HA independent, and murine NK cells recognize and distinguish between Influenza and HIV VLPs that differ solely in protein content. Immunization with UV VSV also prolonged the survival of Rag-KO mice upon lethal challenge. Recognition of DNFB and OXA in B6 mice does not correlate with a specific Ly49 activating receptor, and it was therefore tested whether viral antigens can be recognized by NK in different background strains expressing distinct Ly49 receptors and MHC haplotype. Balb/c Rag-KO mice were immunized and challenged with PR8 or gag/env VLPs, and CHS responses determined. Concurrent with data obtained using B6-Rag-KO mice, Balb/c-KO mice presented with significant CHS responses to PR8 and gag/env VLPs in am antigen specific, CXCR6 dependent manner (FIG. 4g), demonstrating that recognition of Influenza and HIV-derived viral antigens occurs in strains with distinct Ly49 receptors and MHC haplotypes. Concurrent with these findings, immunization with PR8 VLPs significantly prolonged survival of B6 and Balb/c Rag-KO mice upon life virus challenge in a sensitization dependent, antigen specific manner, even when mice were challenged with 200 times the lethal dose of that of a balb/c WT mouse. Importantly and concurrent with all previous data, immunization induced prolonged survival post Influenza challenge, and CHS responses to Influenza A and HIV VLPs were dependent on CXCR6 (FIG. 4h).

In sum, sensitized, hepatic NK cells mediate antigen specific memory responses to at least five distinct antigens, DNFB, OXA, Influenza A (PR8 or M1), HIV VLPs and VSV, and NK cell mediated adaptive immunity requires CXCR6 expression on adaptive NK.

Since NK cell mediated CHS and memory responses to hapten antigens were dependent on CXCR6-expression on NK cells, the role of CXCR6 during NK cell mediated antiviral responses was tested. Rag-KO mice were immunized with indicated VLPs or UV killed virus, and treated with 100 ug anti-CXCR6 or isotype control 24 hrs post challenge. Concurrent with hapten data, NK cell mediated CHS responses to UV VSV, PR8, M1 or gag/env VLPs were all dependent on CXCR6, as blocking antibody, but not isotype control, completely abrogated CHS responses to all four viral antigens (FIG. 4f). Likewise, immunization dependent prolonged survival of Rag-KO mice to lethal Influenza A (FIG. 4e) or VSV challenge was abrogated completely by administration of anti CXCR6, but not isotype control mAb.

Figure 9A:
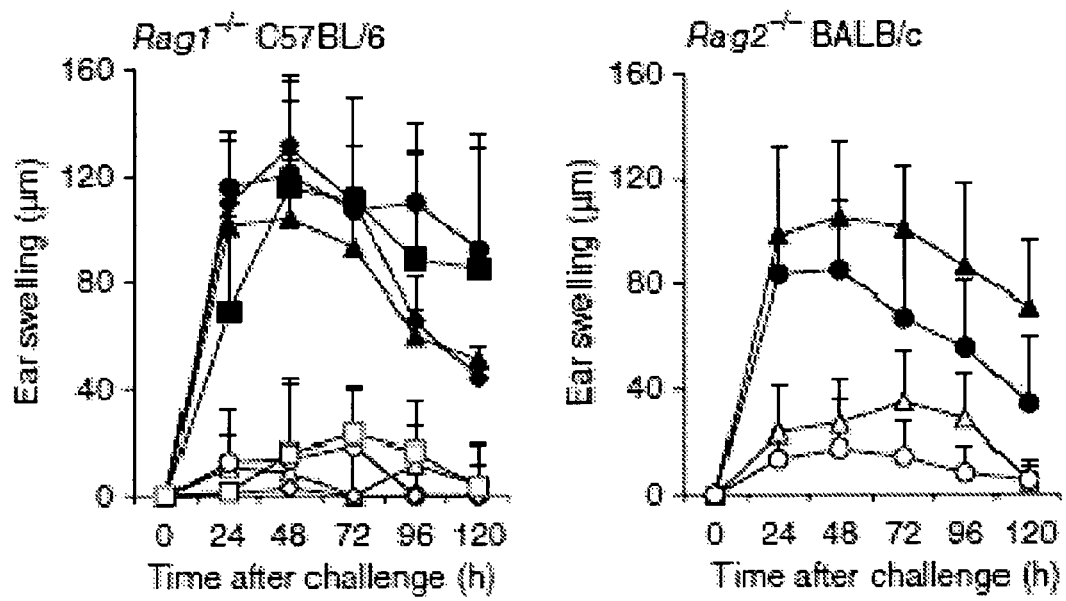
Figure 9B:
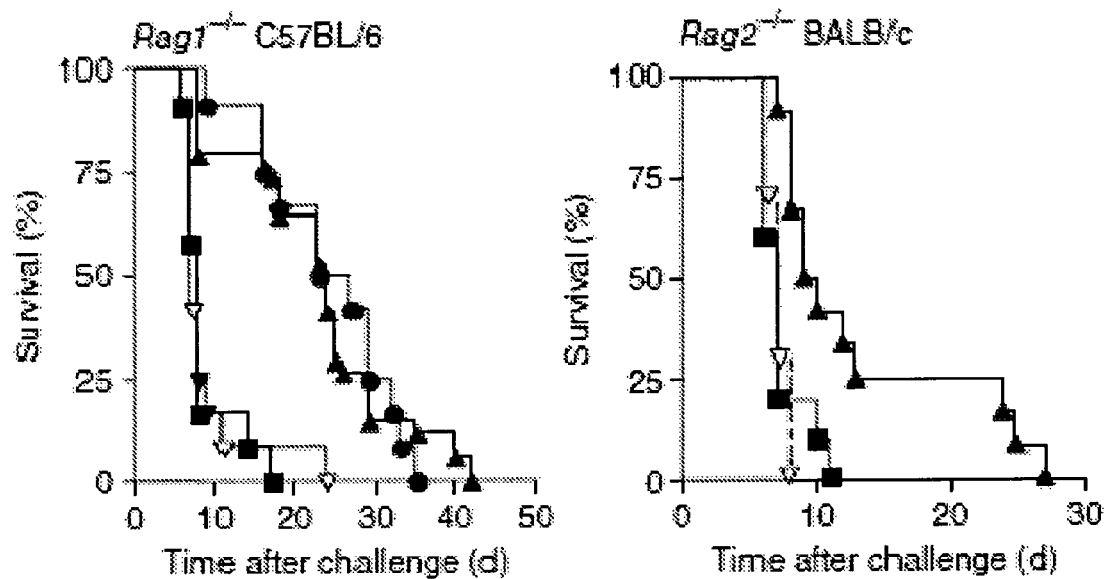

In addition, the effect of administering antibody 12 h prior to challenge was also tested. We sensitized Rag1−/− mice to UV-VSV or to VLPs containing influenza or HIV-1 and treated the mice with anti-CXCR6 or isotype-matched control antibody 12 h before challenging them by injecting viral recall antigen into one ear and PBS into the other. The ensuing DTH response was abolished after CXCR6 blockade regardless of the type of viral antigen or the MHC class I haplotype of the mice (FIG. 9a). Furthermore, anti-CXCR6 abolished the protective effect of memory NK cells after lethal challenge with influenza or VSV (FIG. 9b). Thus, for each of the five antigenic entities tested, CXCR6 was essential for NK cell-mediated adaptive immunity regardless of the genetic background.

Example 6. Role of CXCR6 in the Homeostasis of Memory NK Cells

CXCR6 may exert this critical activity, at least in part, by regulating the homeostasis of hepatic NK cells, similar to its role in the survival of hepatic NKT cells. Steady-state livers of Cxcr6-xc mice contained normal numbers of GFP-NK cells but significantly fewer GFP+ NK cells than did those of Crcr6+/− mice (not shown), and the frequency of the small fraction of GFP+ NK cells in other organs was the same for both genotypes. Thus, CXCR6 is required for the development and/or survival of CXCR6+ NK cells exclusively in the liver, where CXCL16 is constitutively expressed. Furthermore, 4 weeks after adoptive transfer of equal numbers of GFP+ and GFP− hapten-sensitized NK cells from Cxcr6+/− donors, the GFP-NK cells were distributed equally in spleen and liver, whereas the distribution of the GFP+ subset was strongly biased toward the liver (not shown). Moreover, when we transferred equal numbers of GFP+ and GFP− hepatic NK cells sorted from. Cxcr6-xc or Cxcr6+/− donors, the Cxcr6+/− NK cell populations expanded in the livers of Rag2-agIl2rg-12 recipients regardless of their GFP expression, whereas in recipients of CXCR6-deficient NK cells, only the GFP-subset expanded, whereas GFP+NK cells were very rare (not shown). Furthermore, adoptive transfer of DNFB-primed GFP+ hepatic NK cells to naive hosts conferred hapten responsiveness only when NK cells were from Cxcr6+/− donors, whereas the same number of Cxcr6-xc NK cells did not transfer hapten sensitivity (not shown) and survived poorly even after rechallenge with DNFB (not shown).

Example 7. CXCR6 Blockade Inhibits IFN Gamma Production by Antigen Stimulated NK Cells Stimulated or naïve NK cells were cocultured with hapten conjugated (DNBS) B cells. DNBS stimulated NK cells produced more interferon gamma than DNBS naïve NK cells. Moreover, the amount of IFN produced by the NK cells, whether naïve or stimulated, was reduced in the presence of an agent which blocks CXCR6, i.e., anti-CXCR6 or anti-CXCL16 (FIG. 10). This is in contrast to the effect of blockade of the CXCR6-CXCL16 pathway on NK mediated cell killing; as demonstrated above, blockade of the pathway significantly enhanced the cytotoxicity of sensitized hepatic NK cells.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of decreasing antigen-specific NK cell function in a subject comprising:
   measuring antigen-specific NK cell function in the subject and comparing the level of antigen-specific NK cell function to an appropriate control; and
   administering to the subject having an increased level of antigen-specific NK cell function a composition comprising an antibody, or antigen-binding fragment thereof, that binds to an extracellular domain of human CXCR6 and blocks the binding of CXCR6 to the extracellular domain of CXCL16, such that antigen-specific NK cell function is decreased.

2. A method of decreasing antigen-specific NK cell function in a subject having unwanted immune cell activation, comprising:
   measuring antigen-specific NK cell function in the subject and comparing the level of antigen-specific NK cell function to an appropriate control; and administering to the subject having an increased level of antigen-specific NK cell function a composition comprising an antibody, or antigen-binding fragment thereof, that binds to the extracellular domain of CXCL16 and blocks the binding of CXCL16 with an extracellular domain of CXCR6, such that antigen-specific NK cell function is decreased.

3. The method of claim 1 or 2, wherein the subject has delayed-type hypersensitivity to an antigen or is at risk for developing delayed-type hypersensitivity to an antigen.

4. The method of claim 3, wherein the antigen is a hapten.

5. The method of claim 3, wherein the step of administering is performed after secondary exposure to the antigen and prior to the onset of a delayed-type hypersensitivity reaction.

6. The method of claim 3, wherein the step of administering is performed after secondary exposure to the antigen and after onset of a delayed-type hypersensitivity reaction.

7. The method of claim 3, wherein the step of administering is performed prior to secondary exposure to the antigen.

8. The method of claim 1 or 2, wherein the subject suffers from an occupational allergy.

9. The method of claim 1 or 2, wherein the step of administering is performed more than once.

10. The method of claim 1 or 2, further comprising administration of an immunosuppressive agent that inhibits activation of T cells and/or B cells.

11. The method of claim 10, wherein the subject does not respond adequately to said immunosuppressive agent when administered alone.

12. The method of claim 1 or 2, wherein the subject has or is at risk for developing a deleterious immune response to an infectious agent.

13. The method of claim 12, wherein the infectious agent is a virus.

14. The method of claim 12, wherein the infectious agent is a bacteria.

15. The method of claim 12, wherein the infectious agent is a virus selected from the group consisting of: hepatitis B virus, influenza virus, hepatitis C virus, varicella zoster, herpes virus, HIVI and HIV2.

16. A method of treating a subject having delayed-type hypersensitivity to an antigen, comprising:

administering to the subject (i) a composition comprising an antibody, or antigen-binding fragment thereof, wherein the antibody, or antigen-binding fragment thereof, is selected from the group consisting of an antibody, or antigen-binding fragment thereof, that binds to the extracellular domain of CXCR6 and blocks the binding of CXCR6 to CXCL16, and an antibody, or antigen-binding fragment thereof, that binds to the extracellular domain of CXCL16 and blocks the binding of CXCL16 to CXCR6; and (ii) a composition comprising an immunosuppressive agent that inhibits activation of T cells and/or B cells, wherein the immunosuppressive agent is not an antibody, or antigen-binding fragment thereof, that binds CXCR6 or CXCL16, such that hypersensitivity to the antigen is reduced.

17. The method of claim 16, wherein the delayed-type hypersensitivity is due to an occupational allergy.

* * * * *

UNITED STATES PATENT AND TRADEMARK OFFICE
CERTIFICATE OF CORRECTION

PATENT NO. : 9,872,905 B2
APPLICATION NO. : 13/512754
DATED : January 23, 2018
INVENTOR(S) : Ulrich Von Andrian et al.

It is certified that error appears in the above-identified patent and that said Letters Patent is hereby corrected as shown below:

In the Specification

At the Column 1, Line number 12, replace "Work described herein was supported, at least in part, under grant AIO69259 awarded by the National Institutes of Health. The U.S. government, therefore, has certain rights in the invention" to -- This invention was made with government support under AI069259 awarded by the National Institutes of Health. The government has certain rights in the invention. --.

Signed and Sealed this
Sixteenth Day of April, 2024

*Katherine Kelly Vidal*

Katherine Kelly Vidal
*Director of the United States Patent and Trademark Office*